US012741933B2

(12) United States Patent
Jha et al.

(10) Patent No.: US 12,741,933 B2
(45) Date of Patent: Sep. 22, 2026

(54) SMALL MOLECULE NICOTINAMIDE ADENINE DINUCLEOTIDE MODULATORS

(71) Applicant: THE CLEVELAND CLINIC FOUNDATION, Cleveland, OH (US)

(72) Inventors: Babal Kant Jha, Cleveland, OH (US); James G. Phillips, Cleveland, OH (US); Jaroslaw P. Maciejewski, Cleveland, OH (US); Frederic Joel Reu, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 593 days.

(21) Appl. No.: 18/030,105

(22) PCT Filed: Oct. 18, 2021

(86) PCT No.: PCT/US2021/055467
§ 371 (c)(1),
(2) Date: Apr. 4, 2023

(87) PCT Pub. No.: WO2022/082114
PCT Pub. Date: Apr. 21, 2022

(65) Prior Publication Data

US 2023/0331663 A1 Oct. 19, 2023

Related U.S. Application Data

(60) Provisional application No. 63/092,803, filed on Oct. 16, 2020.

(51) Int. Cl.

| | |
|---|---|
| ***C07C 235/84*** | (2006.01) |
| ***A61P 7/00*** | (2006.01) |
| ***C07C 235/64*** | (2006.01) |
| ***C07C 235/66*** | (2006.01) |
| ***C07C 237/40*** | (2006.01) |

(52) U.S. Cl.
CPC .......... *C07C 235/84* (2013.01); *C07C 235/66* (2013.01)

(58) Field of Classification Search
CPC ... C07C 235/84; C07C 235/66; C07C 235/64; C07C 237/40; A61P 7/00
See application file for complete search history.

(56) References Cited

U.S. PATENT DOCUMENTS

| | | | | |
|---|---|---|---|---|
| 4,590,301 | A | 5/1986 | Lim et al. | |
| 2011/0275635 | A1 | 11/2011 | Brouillette | |
| 2017/0057910 | A1* | 3/2017 | Reu | C07C 235/64 |

FOREIGN PATENT DOCUMENTS

| | | | |
|---|---|---|---|
| WO | 2019138323 | A1 | 7/2019 |

OTHER PUBLICATIONS

STN CAS Registry RN 1036456-49-1 (Entered STN date: Jul. 27, 2008). (Year: 2008).*
International Application Published Under the Patent Cooperation Treaty (PCT) with an international publication date of Apr. 21, 2022 corresponding to International Publication No. WO2022/08214A1; pp. 1-58; with International Search Report to corresponding application No. PCT/US21/55467.
PubCham—SID—336187594, Modify Date: Mar. 14, 2014 (Mar. 14, 2014) p. 2, figure, this is a purchasable chemical.
Hogan et al., Front Immunol, 10:1187 (2019).
Adebanjo et al., Nat. Cell Biol. 1 , 409-414 (2009).
Lee, H.C., Ann. Rev. Pharmacol. Toxicol., 41 , 317-345 (2001 ).
Chini et al., Trends Pharmacol Sci., 39(4):424-436 (2018).
Guerreiro et al., Cells, 9(2):471 (2020).
Hong et al., Front Cell Dev Biol., 8:246 (2020).
M. Xiao and D.C. Dooley, Leuk Lymphoma 38(5-6); 489-97 (2000).
Costa et al., Cells, 8(12):1632 (2019).
Savarino et al., AIDS, 14(9):1079-89 (2000).
Horenstein et al., Physiol Rev., 101 (4):1457-1486 (2021 ).

* cited by examiner

*Primary Examiner* — Kamal A Saeed
*Assistant Examiner* — Sagar Patel
(74) *Attorney, Agent, or Firm* — Tarolli, Sundheim, Covell & Tummino LLP

(57) ABSTRACT

Compounds that can be used to increase NAD levels are described by inhibiting NAD+ degrading enzymes such as CD38 are described. The compounds have a structure according to formula I or Formula II, as described herein, or pharmaceutically acceptable salts thereof, wherein the attached groups are as defined in the specification. Methods of increasing intracellular NAD+ levels in a subject by administering an effective amount of a compound according to formula I or formula II to the subject are also described.

1 Claim, 8 Drawing Sheets

Ki = 165 ± 28 nM

Ki = 102 ± 12 nM

Ki = 1822 ± 70 nM

BIOTIN

Ki = 1015 ± 88 nM

NOT DETERMINED

NOT DETERMINED

SMALL MOLECULE NICOTINAMIDE ADENINE DINUCLEOTIDE MODULATORS

CROSS-REFERENCE TO RELATED APPLICATIONS

This application claims priority from U.S. Provisional Application Ser. No. 63/092,803, filed Oct. 16, 2020, which is incorporated herein by reference.

TECHNICAL FIELD

The present disclosure relates generally to small molecule compounds that increase NAD levels as a result of inhibiting NAD-degrading enzymes such as CD38.

BACKGROUND

The human hematopoietic system produces various types of differentiated and short-lived cells with specialized functions, which require continuous replenishment through the function of hematopoietic stem cells (HSC). HSC failure is a common distal endpoint of various pathogenic mechanisms in almost all bone marrow failure (BMF) syndromes and associated diseases. Hematopoietic growth factor cocktails (HGF) used in expanding bone marrow cells e.g., to increase cellularity of the HSC grafts, lead to differentiation and decreased HSC count. Theoretically, when used in vivo, they may act on progenitors rather than HSC and lead to stimulation of clonal outgrowth. The ability to stimulate HSC self-renewal to provide reconstitution of long-term hematopoiesis is currently limited.

Nicotinamide adenine dinucleotide (NAD) serves as an essential cofactor and substrate for a number of critical cellular processes. NAD exists in two forms: an oxidized and a reduced form, abbreviated as $NAD^+$ and NADH, respectively, with $NAD^+$ being the prevalent form under physiological conditions. NAD depletion may occur in response to DNA damage due to free radical/ionizing radiation attack, resulting in significant activation of NAD consuming poly(ADP-ribose) polymerases (PARPs). Because of their long lifespan, maintenance of the genomic integrity of HSCs by efficient and accurate DNA repair to reduce the risk of BMF and cellular transformation is essential. NAD is also required for the maintenance of sirtuins activity, important class Ill HDAC essential for the prevention of senescence. Aging or chronic immune activation and inflammatory cytokine production result in up-modulation of NAD degrading enzyme cluster of differentiation 38 (CD38) that rapidly depletes cellular and extracellular levels of NAD. Various lines of evidence suggest that regulation of CD38 NADase activity is essential for maintenance of physiologic NAD levels. Hogan et al., Front Immunol, 10:1187 (2019). Enhancing NAD level can profoundly reduce oxidative cell damage in catabolic tissue, including blood. Consequently, promotion of intracellular NAD by preventing NAD catabolism represents a promising therapeutic strategy for degenerative diseases in general, and BMF and associated diseases in particular.

CD38 inhibition may be a potential therapeutic principle for ex vivo and in vivo expansion of HSC. Decreasing levels of NAD have been linked to aging and stem cell dysfunction, as a key aspect of various BMF syndromes. The strategy of CD38 inhibition to preserve NAD is innovative and a relevant therapeutic strategy.

SUMMARY

The present invention describes the development of a new class of "HSC mimetic" as therapeutics in BMF that addresses the need to improve HSC function. The importance of such drugs is reflected by wide range of potential applications. They include use in ex vivo expansion, marrow regeneration in aplastic anemia (AA), post chemotherapy and hereditary BMF. Regeneration of normal HSC compartment may also decrease occurrence of clonal hematopoiesis of indeterminate potential (CHIP) as a risk factor for development of myelodysplastic syndrome (MDS). Consequently, such agents could find a range of applications including therapy of conditions, such AA and MDS, for which US servicemen, veterans and their families may have particular risk stemming from exposure to various level of radiation from uranium-depleted ammunition, nuclear weapons and propulsion systems and toxic chemical exposure inherent to operation of weaponry/equipment and aging.

The present invention is inspired by the observations of age-associated decline in metabolic flux of NAD+, a major cofactor for normal hematopoiesis and maintenance HSC to develop small molecules that would improve HSC by restoring/increasing NAD+ levels. NAD+ serves as an essential cofactor and substrate for a number of critical cellular processes involving in oxidative phosphorylation, ATP production, epigenetic modulation, intracellular calcium signaling, immunological functions and efficient DNA repair. See FIG. 1.

The present invention provides nicotinamide adenine dinucleotide (NAD) modulating compounds. Compounds can modulate NAD by either increasing or decreasing its levels. NAD, as used herein, can refer to one or both forms of NAD (NAD+ and NADH) as appropriate, as would be understood by those skilled in the art.

In one aspect, the disclosure relates to a compound having the structure of Formula I:

(I)

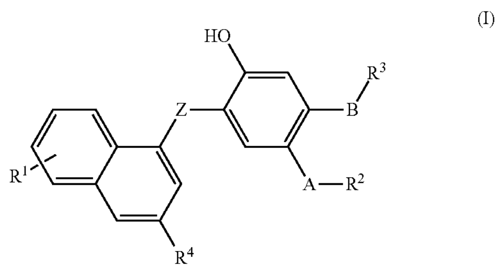

or a pharmaceutically acceptable salt thereof, wherein

A is selected from $C_1$-$C_5$ alkylene wherein one or more of the methylene groups is optionally independently replaced with O, NH, $CF_3$, or S, $C_1$-$C_5$ alkenylene, $C_1$-$C_5$ alkynylene, and

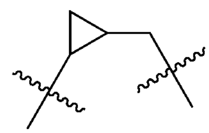;

B is selected from H, $C_1$-$C_5$ alkylene wherein one or more of the methylene groups is optionally independently replaced with O, NH, or S, $C_1$-$C_5$ alkenylene, $C_1$-$C_5$ alkynylene, and

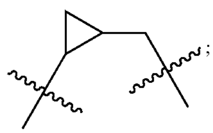 [SMILES: *CC1CC1*]

$R^1$ is selected from H, $CF_3$, COOH, OH, $NH_2$, halogen, $O(C_1$-$C_3$ alkyl), $NHSO_2CH_3$, $CH_2OH$, $CH_2OOH$, $NH(C_1$-$C_3$ alkyl) and

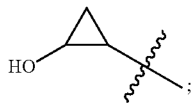 [SMILES: *C1CC1O]

$R^2$ is absent or selected from OH, $NH_2$, COOH, CN, $O(C_1$-$C_3$ alkyl), halogen, $NH(C_1$-$C_3$ alkyl); and

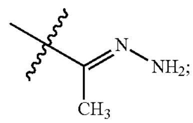

$R^3$ is absent or is selected from OH, $NH_2$, COOH, CN, $O(C_1$-$C_3$ alkyl), halogen, $CF_3$, $NH(C_1$-$C_3$ alkyl) and

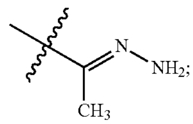

$R^4$ is selected from H, OH, $NH_2$, COOH, halogen, $OCH_3$, $CH_2OH$, $CH_2OOH$, $CF_3$, $(C_1$-$C_5$ alkyl)$NH_2$, $NHSO_2CH_3$ and

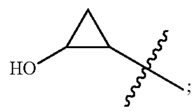 [SMILES: *C1CC1O]

and

Z is selected from NH—C(O), $N(C_1$-$C_5$ alkyl)-C(O), NH—$CH_2$, $N(C_1$-$C_5$ alkyl)-$CH_2$, O—$CH_2$, S—$CH_2$, $CH_2$—$CH_2$, and CH═CH.

In some instances, the disclosure relates to a compound of formula I or a pharmaceutically acceptable salt thereof, wherein B is H; $R^3$ is absent; $R^4$ is H; and $R^2$ is selected from OH, $NH_2$, COOH, CN, $OCH_3$, F, and

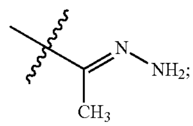

and Z is NH—C(O).

In further instances, $R^1$ is selected from H, $CF_3$, COOH, OH, $NH_2$, F, $OCH_3$, $NHSO_2CH_3$, $CH_2OH$, $CH_2OOH$, and

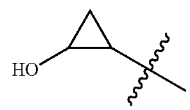

In some instances, the disclosure relates to a compound of formula I or a pharmaceutically acceptable salt thereof, wherein B is H; $R^3$ is absent; $R^4$ is H; $R^1$ is selected from H, $CF_3$, COOH, OH, $NH_2$, F, $OCH_3$, $NHSO_2CH_3$, $CH_2OH$, $CH_2OOH$, and

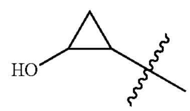

$R^2$ is selected from OH, $NH_2$, COOH, CN, $OCH_3$, F, and

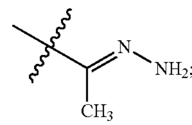

and

A is selected from —$(CH_2)_3$—, —S—$(CH_2)_2$—, —NH—$(CH_2)_2$, —O—$(CH_2)_2$—,

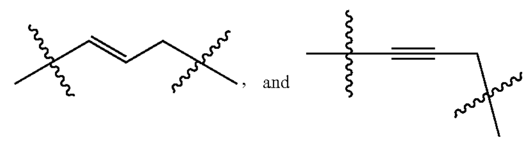

In some instances, the disclosure relates to a compound of formula I or a pharmaceutically acceptable salt thereof wherein B is H; $R^1$ is H; $R^3$ is absent; and Z is NH—C(O).

In some instances, the disclosure relates to a compound of formula I or a pharmaceutically acceptable salt thereof wherein A is selected from $C_1$-$C_3$ alkylene and

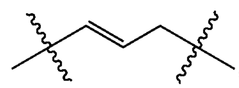

$R^2$ is selected from OH and $NH_2$; B is selected from —$(CH_2)_2$—, —O—$(CH_2)_2$—, and —O—$CH_2$—; $R^3$ is selected from OH and $CF_3$; and Z is NH—C(O).

In some instances, the disclosure relates to a compound of formula I or a pharmaceutically acceptable salt thereof wherein B is H; $R^1$ is H; $R^3$ is absent; $R^4$ is H; and Z is selected from NH—$CH_2$, $N(R_e)$—$CH_2$, O—$CH_2$, S—$CH_2$, $CH_2$—$CH_2$, and CH═CH.

Another aspect of the disclosure relates to a compound having the structure of formula II:

(II)

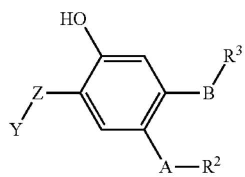

or a pharmaceutically acceptable salt thereof, wherein

Y is selected from

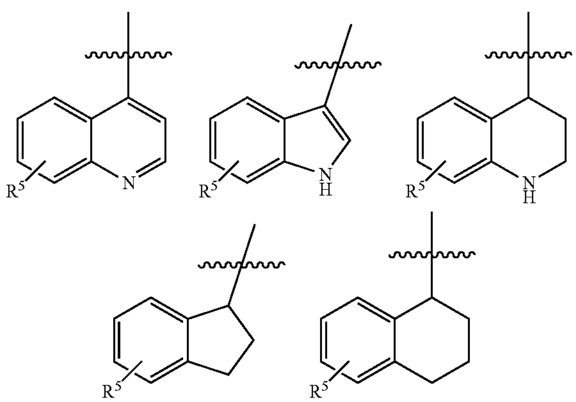

A is selected from $C_1$-$C_8$alkylene wherein one or more of the methylene groups is optionally independently replaced with O, NH, or S, $C_1$-$C_5$ alkenylene, $C_1$-$C_5$ alkynylene, and

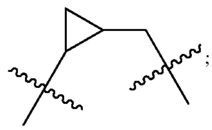

B is selected from H, $C_1$-$C_5$ alkylene wherein one or more of the methylene groups is optionally independently replaced with O, NH, or S, $C_1$-$C_5$ alkenylene, $C_1$-$C_5$ alkynylene, and

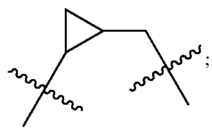

$R^2$ is selected from OH, $NH_2$, COOH, CN, O($C_1$-$C_3$ alkyl), halogen, NH($C_1$-$C_3$ alkyl); and

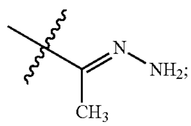 [SMILES: */C(C)=N/N]

$R^3$ is absent or is selected from OH, $NH_2$, COOH, CN, O($C_1$-$C_3$ alkyl), halogen, $CF_3$, NH($C_1$-$C_3$ alkyl) and

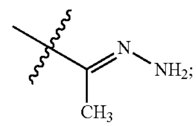 [SMILES: */C(C)=N/N]

$R^5$ is selected from H, $CF_3$, COOH, OH, $NH_2$, halogen, O($C_1$-$C_3$ alkyl), $NHSO_2CH_3$, $CH_2OH$, $CH_2OOH$, NH($C_1$-$C_3$ alkyl) and

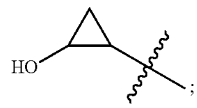 [SMILES: *C1CC1O]

Z is selected from NH—C(O), N($C_1$-$C_8$alkyl)-C(O), NH—$CH_2$, N($C_1$-$C_8$alkyl)-$CH_2$, O—$CH_2$, S—$CH_2$, $CH_2$—$CH_2$, and CH═CH.

In some instances, the disclosure relates to a compound of formula II or a pharmaceutically acceptable salt thereof wherein Z is NH—C(O).

Another aspect of the present disclosure provides a method of increasing intracellular NAD levels in a subject in need thereof, comprising administering an effective amount of a compound according to formula I or formula I to the subject. In some embodiments, the compound inhibits CD38. In further embodiments, the subject has been diagnosed with a degenerative disease. In yet further embodiments, the subject has been diagnosed with bone marrow failure.

The present disclosure also relates to the discovery that certain inhibitors of the CD38 enzyme (or related enzymes) can be used for treating diseases or conditions where CD38 is over expressed or where elevating NAD levels will have beneficial effects. In some instances CD38 inhibitors discloses herein can be used to combat aging and can be used in the prevention of age related senescence and replicative exhaustion. In some instances the CD38 inhibitors can be used to treat infection, such as tuberculosis infection and intracellular mycobacterial infections. In some instances the CD38 compounds may be used to treat HIV. The CD38 inhibitors disclosed herein can also be used to treat and/or prevent certain types of cancer including myeloma and lymphoma. Additionally, the CD38 inhibitors disclosed herein may also be used in the treatment of diseases or conditions where stem cell maintenance and expansion is beneficial.

BRIEF DESCRIPTION OF THE DRAWINGS

The foregoing and other features of the present disclosure will become apparent to those skilled in the art to which the present disclosure relates upon reading the following description with reference to the accompanying drawings, in which.

Compound 1-17 bound to the CD38 with highest DG binding. A. Ribbon diagram and B. Hydrophobic surface rendering. The complex was energy minimized using Chimera 1.8.0

FIGS. 3A-3D provides graphs showing Compound 1-17 inhibits CD38 and protects NAD degradation in vitro. Full length wild type recombinant CD38 was expressed and purified and incubated with NAD and high-performance liquid chromatographic assay using $C_{18}$ were used to quantify NAD degradation. A. chromatogram with vehicle, B. CD38 incubation for 4 hours at room temperature C. CD 38 degradation of NAD as measured by ADPR D. Dose dependent inhibition of CD38.

Figures 4A, 4B:
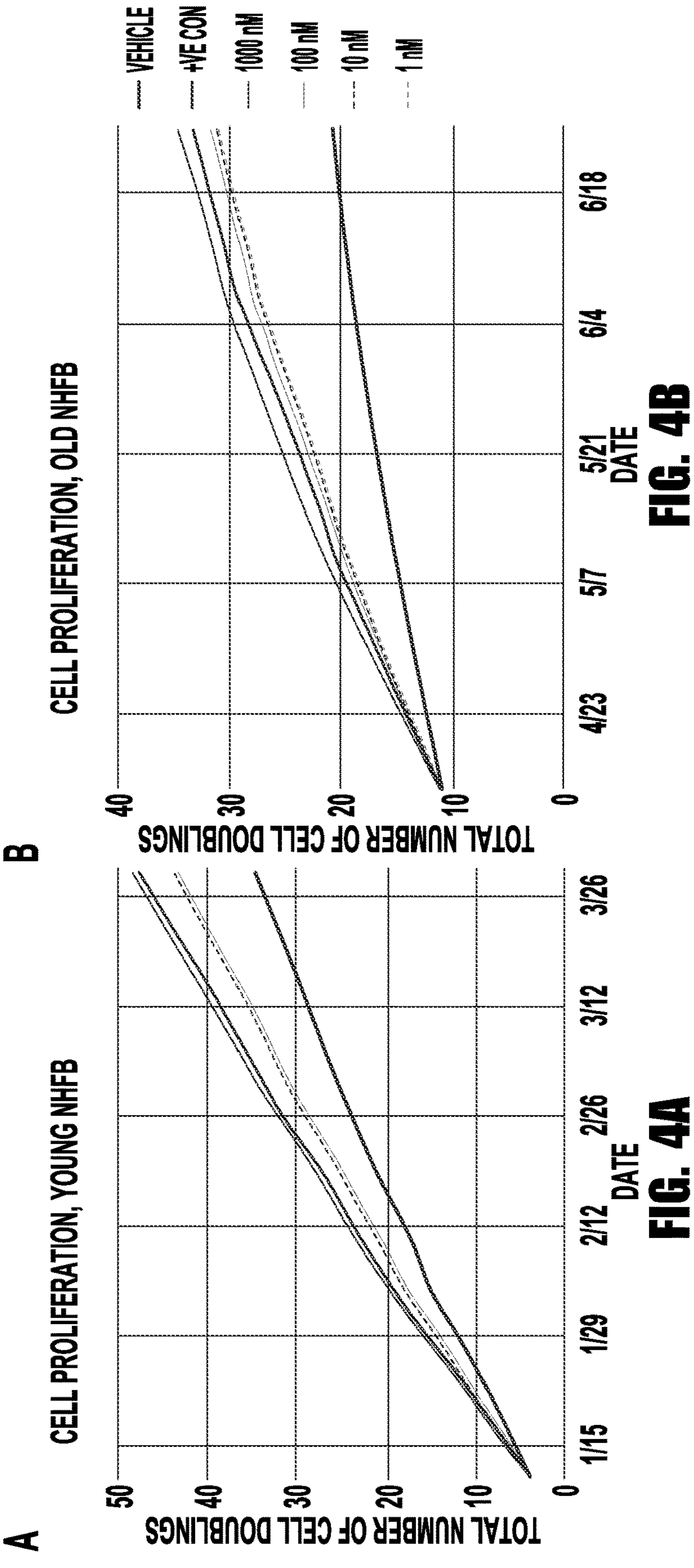

FIGS. 4A and 4B provide graphs showing NAD protection by compound 1-17 extend life span of undifferentiated normal human fibroblast (NHFB) under in-vitro cell culture conditions. NHFB were either A. young (<8 doubling time) or B. old (>10 doublings) cell cultures were treated with indicated amount of 1-17 in complete growth media. The doubling time significantly increased in a dose dependent fashion.

Figure 5B:
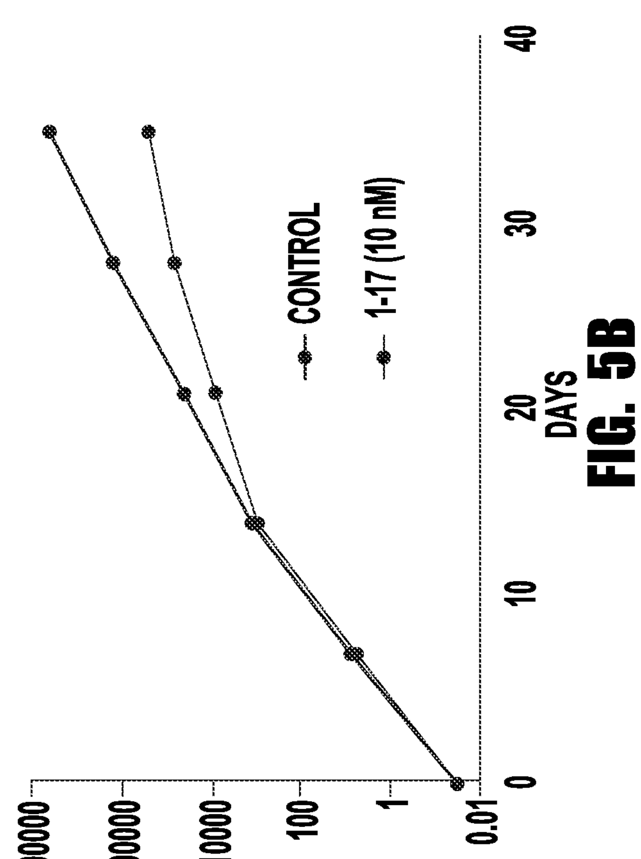
Figure 5A:
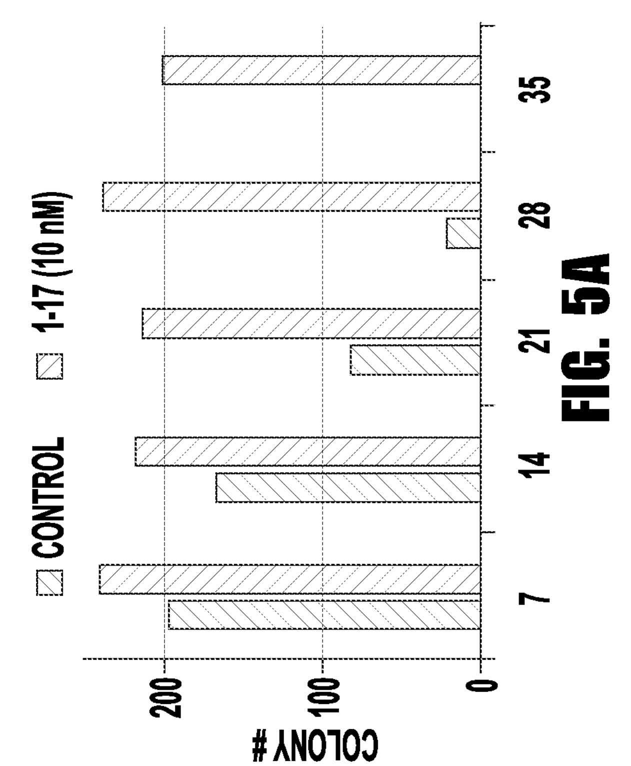

FIGS. 5A and 5B provide graphs showing Treatment of 1-17 to murine bone marrow expands the colony forming hematopoietic stem cells. The murine bone marrow cells from C57BL6 mice were grown in methyl cellulose in the presence and absence of the compound 1-17 and colony number were counted every week and re-plated. A. The number of colony and B. the total cellular output.

Figure 6B:
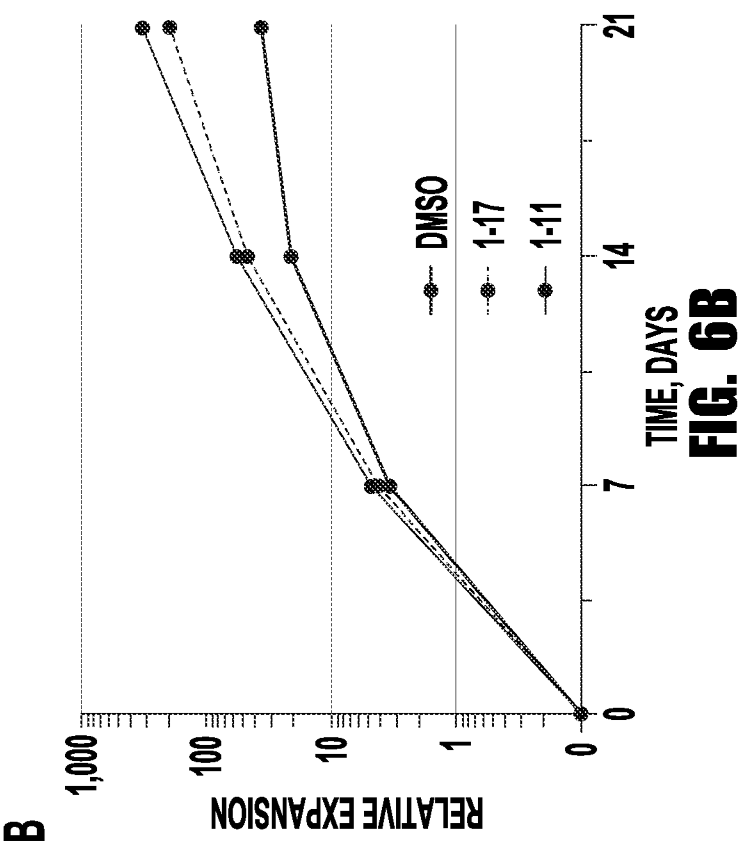
Figure 6A:
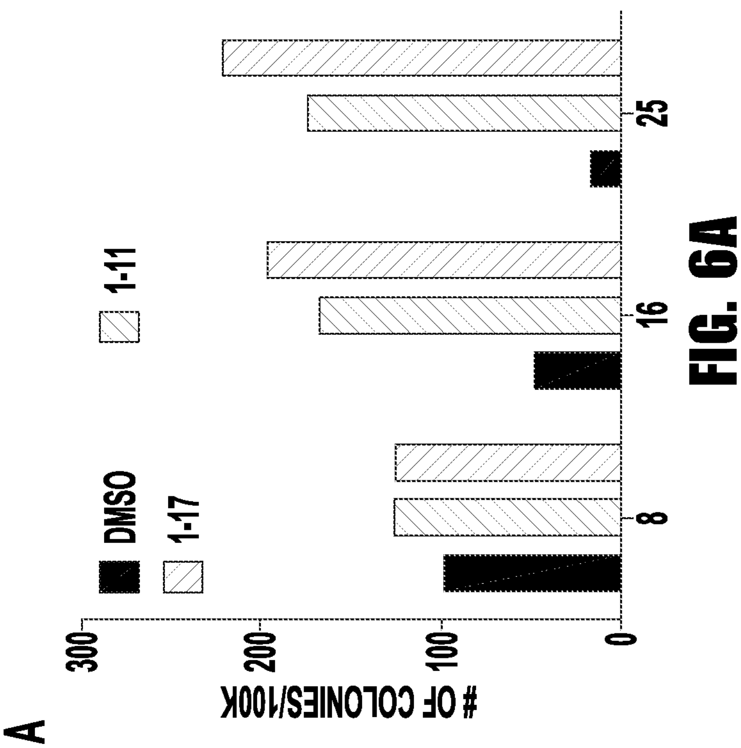
Figures 7A, 7B, 7C, 7D:
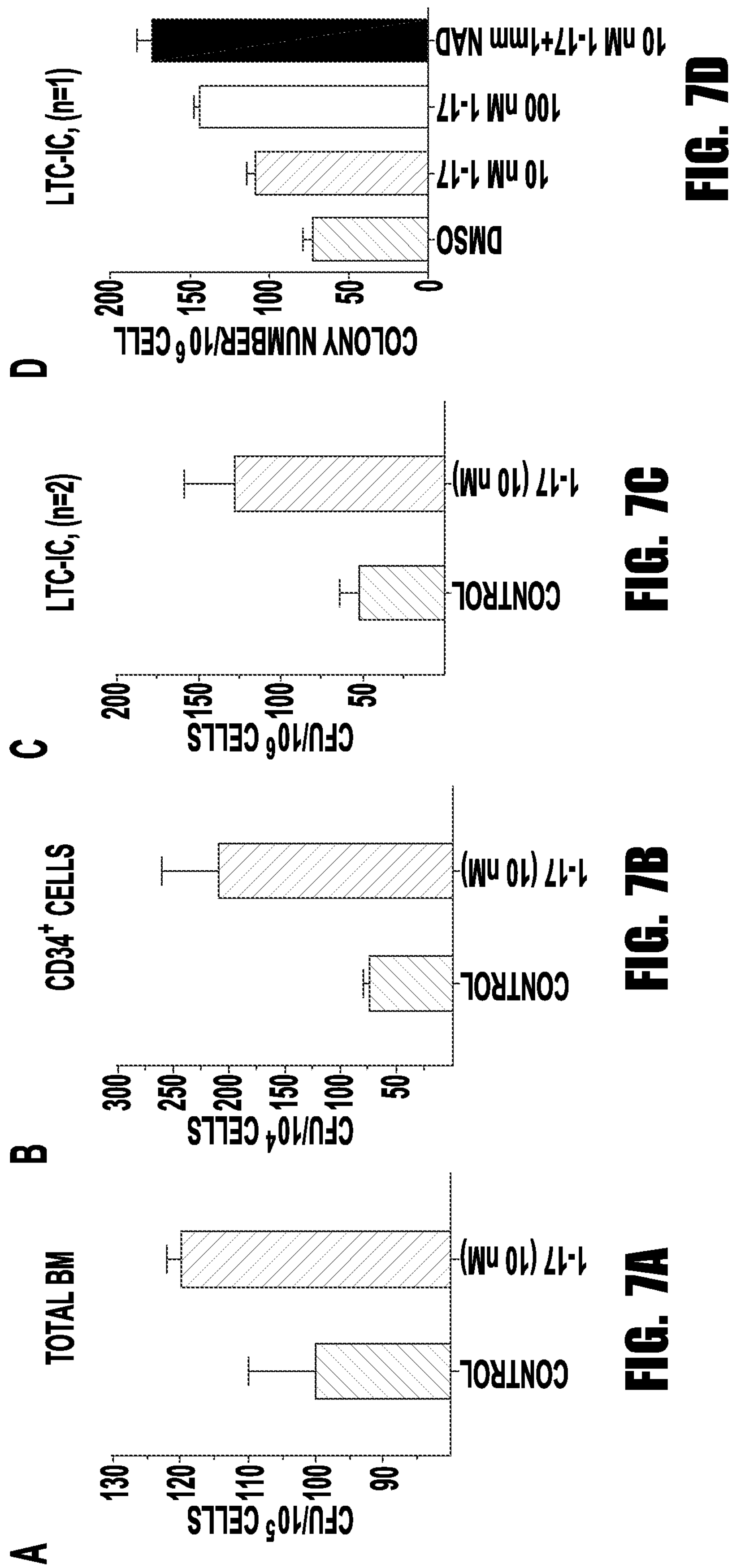

FIGS. 6A and 6B provide graphs showing administration of 1-17 to human bone marrow expands the colony forming hematopoietic stem and progenitor cells (HSPCs). The human bone marrow cells from healthy volunteers were grown in methyl cellulose in the presence and absence of the compound 1-17 and colony number were counted after eight days in culture and re-plated till control HSPCs were completely exhausted. A. The number of colony and B. the total cellular output.

FIGS. 7A-7D provide graphs showing the compound 1-17 treatment expands long term hematopoietic stem cells in cell culture. Total Human bone marrow A, isolated CD34+ HSPCs B, and long-term culture initiating hematopoietic cells (LTC-IC) C, were grown in the presence and absence of the compound 1-17 and the total cellular output was determined. Compound 1-17 is synergistic with NAD treatment.

Figures 8A, 8B, 8C:
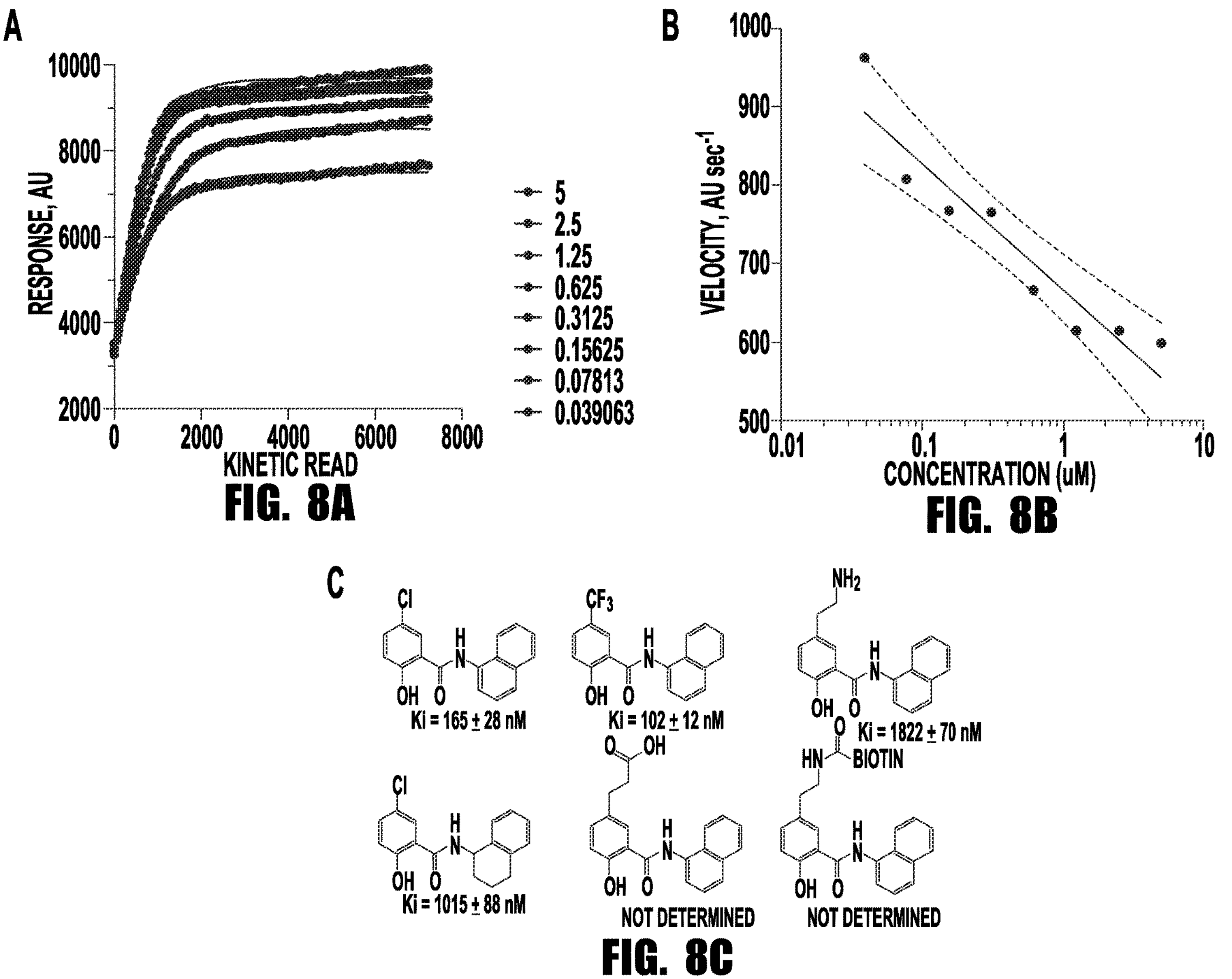

FIGS. 8A-8C provide graphs and chemical structures showing the determination of the inhibition equilibrium constant Ki for various CD38 inhibiting compounds. FIG. 8A provides a graph showing the kinetics of CD38 activity in the presence of different concentrations of the inhibitors; FIG. 8B shows calculation of Ki from the slope of the semi log fit curve of the velocity, determined by reaction progress curve at different inhibitor concentrations; and FIG. 8C provides the structures of a number of the compounds that were tested.

DETAILED DESCRIPTION

1. Definitions

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

The term "alkyl" refers to a saturated aliphatic hydrocarbon monovalent radical having the specified number of carbon atoms. For example, $C_1$-$C_4$ alkyl, is intended to include a hydrocarbon chain that includes between 1 and 4 carbon atoms. Unless otherwise indicated, any alkyl radical can be linear or branched. Exemplary alkyl radicals include methyl, ethyl, propyl, isopropyl, n-butyl, t-butyl, sec-butyl, iso-butyl, and the like.

The term "alkenyl" refers to an unsaturated hydrocarbon monovalent radical having one or more carbon-carbon double bonds and the specified number of carbon atoms. Unless otherwise indicated, any alkenyl can be monounsaturated or polyunsaturated alkenyl.

The term "alkynyl" refers to an unsaturated hydrocarbon monovalent radical having one or more carbon-carbon triple bonds and the specific number of carbon atoms.

The term "alkylene" refers to a saturated aliphatic hydrocarbon diradical (i.e., divalent radical) having the specified number of carbon atoms. Unless otherwise indicated, any alkylene can be linear or branched. For example, $C_1$-$C_7$ alkylene is intended to include a hydrocarbon chain that contains between 1 and 7 carbon atoms. Examples of alkylene groups include, but are not limited to methylene, ethylene, propylene, butylene, pentylene, hexylene, heptylene, and isopropylene.

The term "alkenylene" refers to an unsaturated hydrocarbon diradical having one or more carbon-carbon double bonds and the specific number of carbon atoms. Unless otherwise indicated, alkenylene diradicals can be monounsaturated or polyunsaturated, and can be linear or branched.

The term "alkynylene" refers to an unsaturated hydrocarbon diradical having one or more carbon-carbon triple bonds and the specific number of carbons. Alkynylene diradicals can also have one or more carbon-carbon double bonds. Unless otherwise indicated, alkynylene diradicals can be monounsaturated or polyunsaturated, and can be linear or branched.

The term "aryl" as used herein includes carbocyclic aromatic rings or ring systems. Examples of aryl groups include phenyl, naphthyl, biphenyl, anthracenyl, phenanthracenyl, fluorenyl and indenyl. Aryl groups may be substituted or unsubstituted.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

When a group is present more than once in any formula or scheme described herein, each group (or substituent) is independently selected, whether explicitly stated or not. For example, for the formula $—C(O)—NR_2$ each R group is independently selected.

The term "heteroatom," as used herein, means oxygen, sulfur, or nitrogen,

The term "halogen," as used herein, means chlorine, bromine, fluorine or iodine.

A subject, as defined herein, is an animal such as a vertebrate or invertebrate organism. In some instances, the subject is a single celled organism such as a yeast or bacteria. In other instances, the subject is a mammal such as a domesticated farm animal (e.g., cow, horse, pig) or pet (e.g., dog, cat). In some instances the subject is a human.

Treat", "treating", and "treatment", etc., as used herein, refer to any action providing a benefit to a subject afflicted with a disease or condition including improvement in the condition through lessening or suppression of at least one symptom, delay in progression of the disease, etc.

"Pharmaceutically acceptable" as used herein means that the compound or composition is suitable for administration to a subject for the methods described herein, without unduly deleterious side effects in light of the severity of the disease and necessity of the treatment.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses. An effective amount, on the other hand, is an amount sufficient to provide a significant chemical effect.

NAD+ depletion may occur in response to excessive DNA damage due to free radical/ionizing radiation attack, resulting in significant poly(ADP-ribose) polymerase (PARP) activation and a high turnover and subsequent depletion of NAD+. Because of their long lifespan, maintenance of genomic integrity of HSCs by efficient and accurate DNA repair to reduce the risk of either BM failure or transformation is essential. NAD+ is also required in maintenance of proper activity of sirtuins, important deacetylases (Class Ill HDAC) essential for prevention of senescence. Aging, activity of DNA repair and or chronic immune activation and inflammatory cytokine production result in overexpression and accelerated activity of NAD+ degrading enzyme CD38 that rapidly depletes cellular and extracellular levels of NAD+. CD38 is expressed on the cell surface as well as intracellularly. Adebanjo et al., Nat. Cell Biol. 1, 409-414 (2009). Various lines of evidence suggest that CD38 NADase activity is essential for maintenance of physiologic NAD+ levels. Enhancing NAD+ levels can profoundly reduce oxidative cell damage in catabolic tissue, including blood. Consequently, promotion of intracellular NAD+ by preventing the NAD+ catabolism represents a promising therapeutic strategy for degenerative diseases in general, and BMF and associated diseases in particular. CD38, a major NAD+ degrading enzyme can therefore be an excellent therapeutic target to maintain its physiological levels and such agents would improve the function of HSC6. Lee, H. C., Ann. Rev. Pharmacol. Toxicol., 41, 317-345 (2001). The inventors have used a structure guided in-silico approach coupled with rational synthesis to develop a number of CD38 inhibitors.

CD38 Inhibitors

The general scaffold structure of formula I represents derivatives that have been synthesized, subject to biological evaluation, and have similar in-silico docking to the same binding site of the lead compound, compound 1-1.

Docking analysis used for the design of new compounds according to Formula I were synthesized using the methods described herein. These molecules were tested in CD38 activity assays using liquid chromatography mass spectroscopy (LCMS) with purified CD38 protein as wells on other selected NAD+ degrading enzymes like CD157. Cell-permeable forms can be synthesized for in vitro cultures and for in vivo mouse experiments.

In one aspect, the disclosure relates to a compound having the structure of Formula I:

(I)

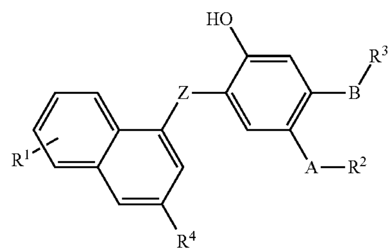

or a pharmaceutically acceptable salt thereof, wherein

A is selected from $C_1$-$C_5$ alkylene wherein one or more of the methylene groups is optionally independently replaced with 0, NH, $CF_3$, or S, $C_1$-$C_5$ alkenylene, $C_1$-$C_5$ alkynylene, and

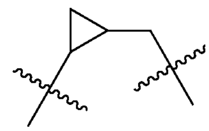;

B is selected from H, $C_1$-$C_5$ alkylene wherein one or more of the methylene groups is optionally independently replaced with O, NH, or S, $C_1$-$C_5$ alkenylene, $C_1$-$C_5$ alkynylene, and

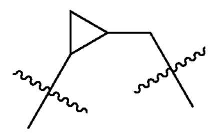;

$R^1$ is selected from H, $CF_3$, COOH, OH, $NH_2$, halogen, $O(C_1$-$C_3$ alkyl), $NHSO_2CH_3$, $CH_2OH$, $CH_2OOH$, $NH(C_1$-$C_3$ alkyl) and

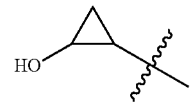;

$R^2$ is absent or is selected from OH, $NH_2$, COOH, CN, $O(C_1$-$C_3$ alkyl), halogen, $NH(C_1$-$C_3$ alkyl); and

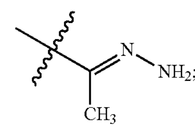;

$R^3$ is absent or is selected from OH, $NH_2$, COOH, CN, $O(C_1-C_3$ alkyl), halogen, $CF_3$, $NH(C_1-C_3$ alkyl) and

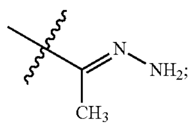

$R^4$ is selected from H, OH, $NH_2$, COOH, halogen, $OCH_3$, $CH_2OH$, $CH_2OOH$, $CF_3$, $(C_1-C_5$ alkyl)$NH_2$, $NHSO_2CH_3$ and

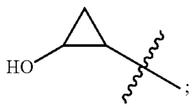 [SMILES: *C1CC1O]

Z is selected from NH—C(O), $N(C_1-C_5$ alkyl)-C(O), NH—$CH_2$, $N(R_e)$—$CH_2$, O—$CH_2$, S—$CH_2$, $CH_2$—$CH_2$, and CH═CH.

In some instances, the alkylene, alkenylene, or alkynylene chains "A" can be further substituted. In some instances the alkylene, alkenylene, or alkynylene chains "B" can be further substituted. In some instances the cyclopropyl ring of

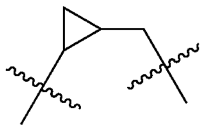 [SMILES: *CC1CC1*]

can be further substituted. For instance, one or more of the hydrogen atoms can be independently replaced with a group selected from alkyl, aryl, arylalkyl, alkoxy, hydroxy, carboxy, acyl, halogen, nitro, cyano, and alkylthio.

In some instances, the disclosure relates to a compound of formula I or a pharmaceutically acceptable salt thereof, wherein B is H; $R^3$ is absent; $R^4$ is H; and $R^2$ is selected from OH, $NH_2$, COOH, CN, $OCH_3$, F, and

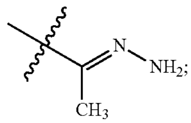

and Z is NH—C(O).

In further instances, $R^1$ is selected from H, $CF_3$, COOH, OH, $NH_2$, F, $OCH_3$, $NHSO_2CH_3$, $CH_2OH$, $CH_2OOH$, and

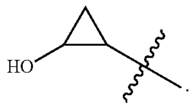 [SMILES: *C1CC1O]

In some instances, the disclosure relates to a compound of formula I or a pharmaceutically acceptable salt thereof, wherein B is H; $R^3$ is absent; $R^4$ is H;

$R^1$ is selected from H, $CF_3$, COOH, OH, $NH_2$, F, $OCH_3$, $NHSO_2CH_3$, $CH_2OH$, $CH_2OOH$, and

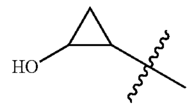

$R^2$ is selected from OH, $NH_2$, COOH, CN, $OCH_3$, F, and

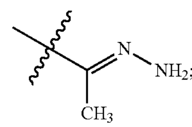

and

A is selected from —$(CH_2)_3$—, —S—$(CH_2)_2$, —NH—$(CH_2)_2$, —O—$(CH_2)_2$—,

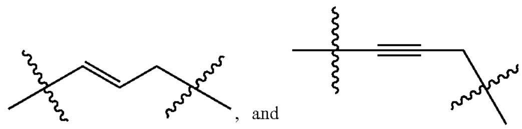

In some instances, the disclosure relates to a compound of formula I or a pharmaceutically acceptable salt thereof wherein B is H; $R^1$ is H; $R^3$ is absent; and Z is NH—C(O).

In some instances, the disclosure relates to a compound of formula I or a pharmaceutically acceptable salt thereof wherein A is selected from $C_1-C_3$ alkylene and

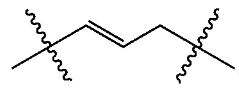

$R^2$ is selected from OH and $NH_2$,

B is selected from —$(CH_2)_2$—, —O—$(CH_2)_2$—, and —O—$CH_2$—;

$R^3$ is selected from OH and $CF_3$; and

Z is NH—C(O).

In some instances, the disclosure relates to a compound of formula I or a pharmaceutically acceptable salt thereof wherein B is H; $R^1$ is H; $R^3$ is absent; $R^4$ is H; and Z is selected from NH—$CH_2$, $N(R_e)$—$CH_2$, O—$CH_2$, S—$CH_2$, $CH_2$—$CH_2$, and CH═CH.

In one aspect, the compound of formula I may be as follows:
| Compound Structure | Compound Designation |
|---|---|
| 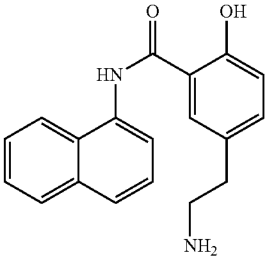 [SMILES: NCCc1ccc(O)c(C(=O)Nc2cccc3ccccc23)c1] | 1-1 |
| 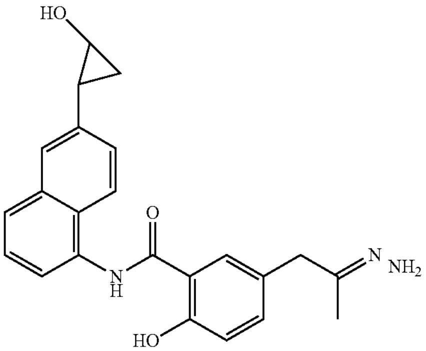 | 1-2 |
| 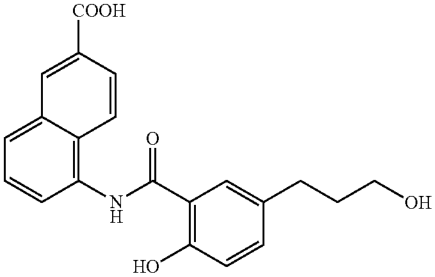 [SMILES: O=C(O)c1ccc2c(NC(=O)c3cc(CCCO)ccc3O)cccc2c1] | 1-3 |
| 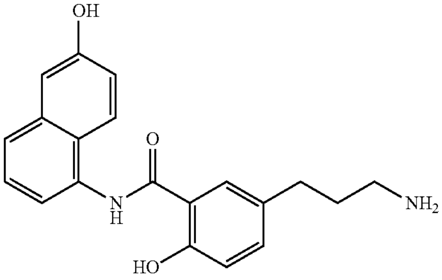 [SMILES: NCCCc1ccc(O)c(C(=O)Nc2cccc3cc(O)ccc23)c1] | 1-4 |
| 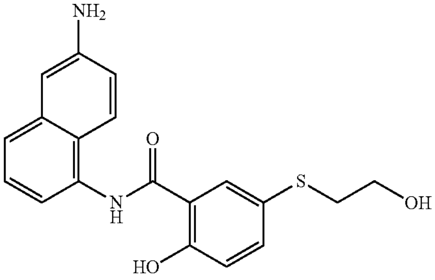 [SMILES: Nc1ccc2c(NC(=O)c3cc(SCCO)ccc3O)cccc2c1] | 1-5 |
-continued
| Compound Structure | Compound Designation |
|---|---|
| 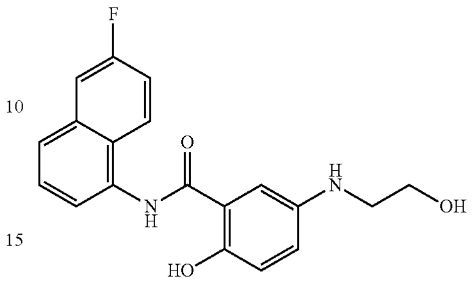 | 1-6 |
| 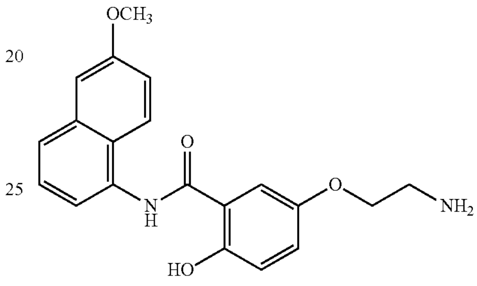 | 1-7 |
| 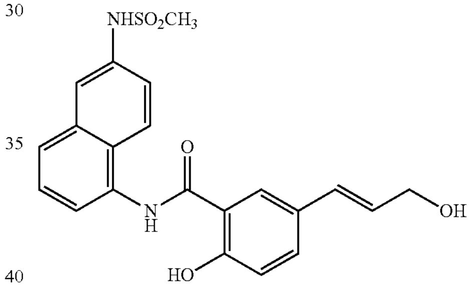 | 1-8 |
| 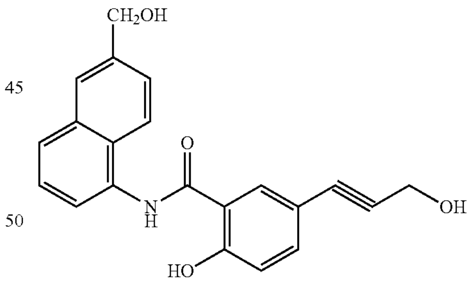 | 1-9 |
| 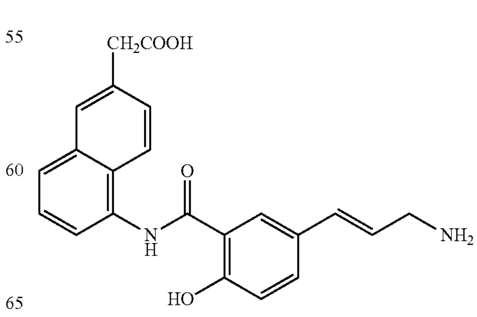 | 1-10 |

-continued
| Compound Structure | Compound Designation |
|---|---|
| 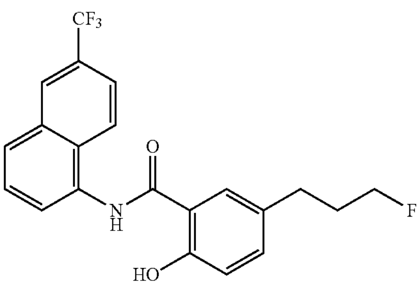 [SMILES: O=C(Nc1cccc2cc(C(F)(F)F)ccc12)c1cc(CCCF)ccc1O] | 1-11 |
| 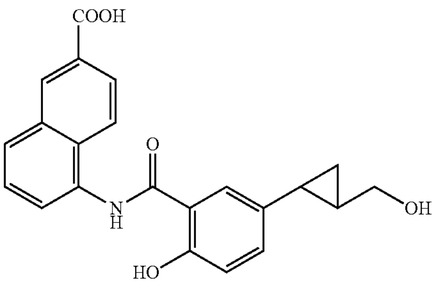 [SMILES: O=C(O)c1ccc2c(NC(=O)c3cc(C4CC4CO)ccc3O)cccc2c1] | 1-12 |
| 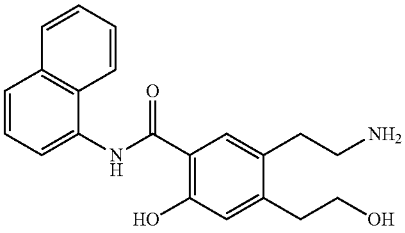 [SMILES: NCCc1cc(C(=O)Nc2cccc3ccccc23)c(O)cc1CCO] | 1-13 |
| 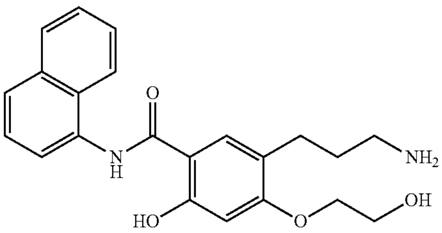 [SMILES: NCCCc1cc(C(=O)Nc2cccc3ccccc23)c(O)cc1OCCO] | 1-14 |
| 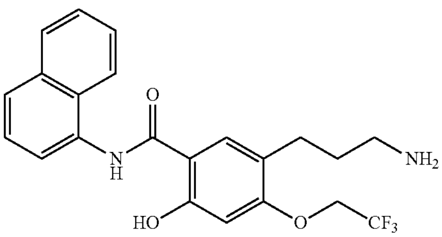 [SMILES: NCCCc1cc(C(=O)Nc2cccc3ccccc23)c(O)cc1OCC(F)(F)F] | 1-15 |
| 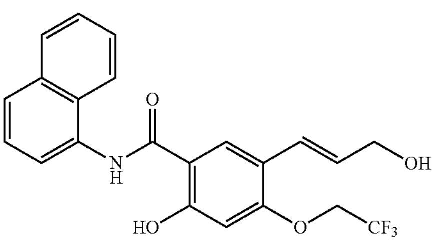 [SMILES: O=C(Nc1cccc2ccccc12)c1cc(/C=C/CO)c(OCC(F)(F)F)cc1O] | 1-16 |
-continued
| Compound Structure | Compound Designation |
|---|---|
| 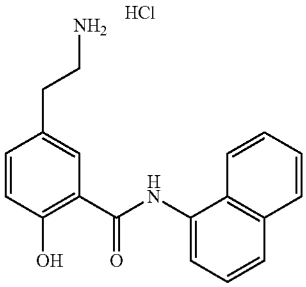 [SMILES: Cl ; NCCc1ccc(O)c(C(=O)Nc2cccc3ccccc23)c1] | 1-17 |
| 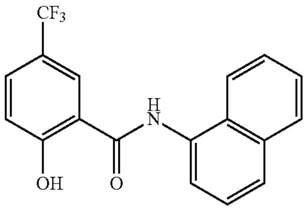 [SMILES: O=C(Nc1cccc2ccccc12)c1cc(C(F)(F)F)ccc1O] | 1-18 |
| 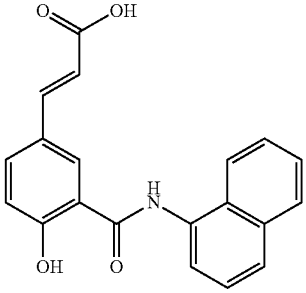 [SMILES: O=C(O)/C=C/c1ccc(O)c(C(=O)Nc2cccc3ccccc23)c1] | 1-19 |
Another aspect of the disclosure relates to a compound having the structure of formula II:
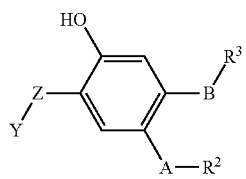
(II)
or a pharmaceutically acceptable salt thereof, wherein
Y is selected from
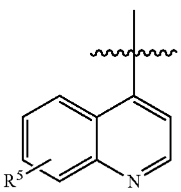 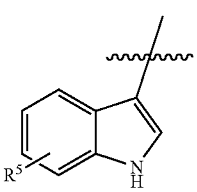 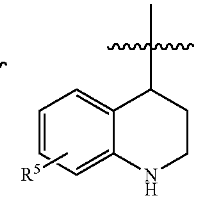

-continued

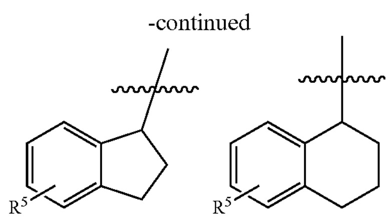

A is selected from $C_1$-$C_5$ alkylene wherein one or more of the methylene groups is optionally independently replaced with O, NH, or S, $C_1$-$C_5$ alkenylene, $C_1$-$C_5$ alkynylene, and

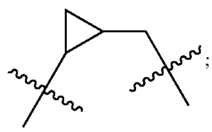 [SMILES: *CC1CC1*]

B is selected from H, $C_1$-$C_5$ alkylene wherein one or more of the methylene groups is optionally independently replaced with O, NH, or S, $C_1$-$C_5$ alkenylene, $C_1$-$C_5$ alkynylene, and

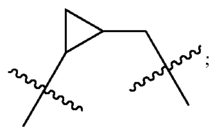 [SMILES: *CC1CC1*]

$R^2$ is selected from OH, $NH_2$, COOH, CN, O($C_1$-$C_3$ alkyl), halogen, NH($C_1$-$C_3$ alkyl); and

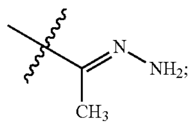

$R^3$ is absent or is selected from OH, $NH_2$, COOH, CN, O($C_1$-$C_3$ alkyl), halogen, $CF_3$, NH($C_1$-$C_3$ alkyl) and

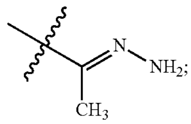

$R^5$ is selected from H, $CF_3$, COOH, OH, $NH_2$, halogen, O($C_1$-$C_3$ alkyl), $NHSO_2CH_3$, $CH_2OH$, $CH_2OOH$, NH($C_1$-$C_3$ alkyl) and

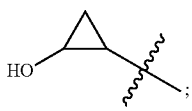 [SMILES: *C1CC1O]

Z is selected from NH—C(O), N($C_1$-$C_5$ alkyl)-C(O), NH—$CH_2$, N($C_1$-$C_5$ alkyl)-$CH_2$, O—$CH_2$, S—$CH_2$, $CH_2$—$CH_2$, and CH═CH.

In some instances, the alkylene, alkenylene, or alkynylene chains "A" can be further substituted. For instance, one or more of the hydrogen atoms can be independently replaced with a group selected from alkyl, aryl, arylalkyl, alkoxy, hydroxy, carboxy, acyl, halogen, nitro, cyano, and alkylthio.

In some instances, the disclosure relates to a compound of formula II or a pharmaceutically acceptable salt thereof wherein Z is NH—C(O).

In further instances, the disclosure relates to a compound of formula II wherein A is a $C_1$-$C_3$ alkyl group or a $C_1$-$C_3$ alkenylene, and $R^2$ is OH or $NH_2$.

In yet further instances, the disclosure relates to a compound of formula II wherein B is H and $R^3$ is absent, or B is O($C_1$-$C_3$ alkyl) and $R^3$ is OH.

In another aspect, the compound of formula II may be as follows:

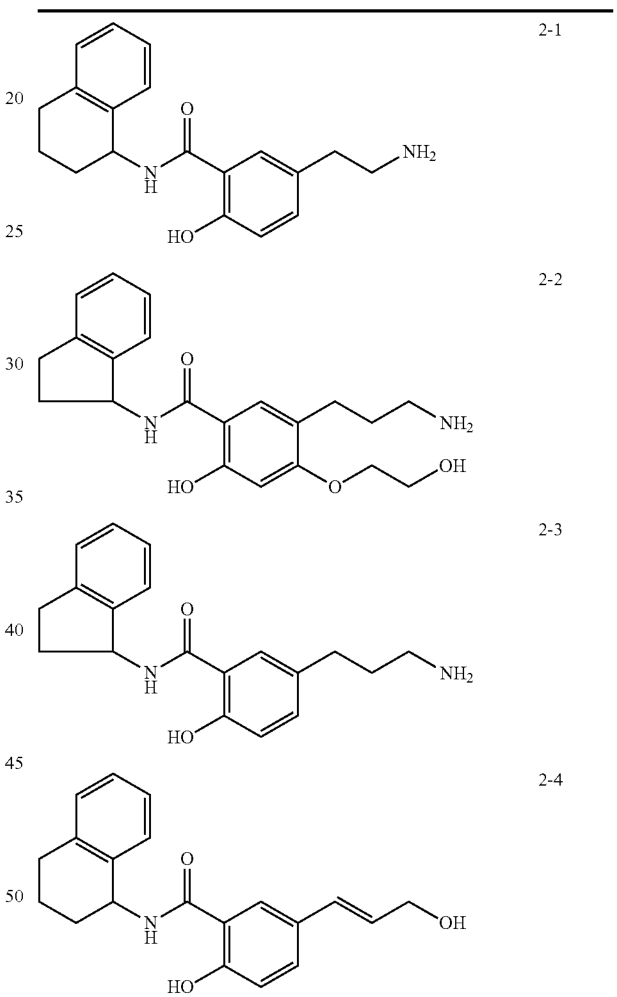

2-1

2-2

2-3

2-4

When the compounds described herein are in the forms of salts, they are preferably pharmaceutically acceptable salts. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

One exemplary salt is the hydrochloride salt of the compound 1-17:

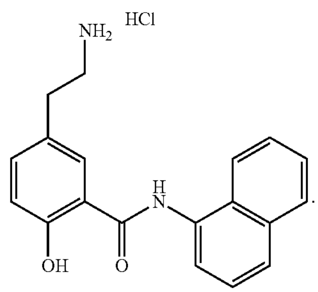 [SMILES: Cl ; NCCc1ccc(O)c(C(=O)Nc2cccc3ccccc23)c1]

Pharmaceutically acceptable salts can be prepared by reacting the compounds disclosed herein with a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol, etc. A mixture of solvents may be used. Organic bases like lysine, arginine, diethanolamine, choline, guanidine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid, salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane, etc. A mixture of solvents may also be used.

The compounds disclosed herein may contain one or more asymmetric carbon atoms, so that the compounds can exist in different stereoisomeric forms. The compounds can be, for example, racemates or optically active forms. The optically active forms can be obtained by resolution of the racemates or by asymmetric synthesis. In some instances, the compounds disclosed herein are R enantiomers. In other instances, the compounds disclosed herein are S enantiomers. In some instances, the compounds disclosed herein are varying mixtures of enantiomers.

Formulations and Administration

The present invention also provides pharmaceutical compositions that include NAD modulating compounds (e.g., CD38 inhibitors) as an active ingredient, and a pharmaceutically acceptable liquid carrier or carriers, in combination with the active ingredient. Any of the compounds of Formula I or Formula II described herein can be included in pharmaceutical compositions of the invention.

The pharmaceutical compositions include CD38 inhibitors together with one or more of a variety of physiological acceptable carriers for delivery to a patient, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the active agent into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The CD38 inhibitors can be administered as a single dose or in multiple doses. Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949.

The CD38 inhibitors are preferably formulated in pharmaceutical compositions and then, in accordance with the methods of the invention, administered to a subject, such as a human patient, in a variety of forms adapted to the chosen route of administration. The formulations include, but are not limited to, those suitable for oral, rectal, vaginal, topical, nasal, ophthalmic, or parental (including subcutaneous, intramuscular, intraperitoneal, intratumoral, and intravenous) administration.

Formulations of the present invention suitable for oral administration may be presented as discrete units such as tablets, troches, capsules, lozenges, wafers, or cachets, each containing a predetermined amount of the active agent as a powder or granules, as liposomes containing CD38 inhibitors, or as a solution or suspension in an aqueous liquor or non-aqueous liquid such as a syrup, an elixir, an emulsion, or a draught. Such compositions and preparations typically contain at least about 0.1 wt-% of the active agent.

The dosage form and amount can be readily established by reference to known treatment or prophylactic regiments. The amount of therapeutically active compound that is administered and the dosage regimen for treating a disease condition with the compounds and/or compositions of this invention depends on a variety of factors, including the age, weight, sex, and medical condition of the subject, the severity of the disease, the route and frequency of administration, and the particular compound employed, the location of the disease, and the pharmacokinetic properties of the individual treated, and thus may vary widely. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administrated may need to be optimized for each individual. The pharmaceutical compositions may contain active ingredient in the range of about 0.1 to 2000 mg, preferably in the range of about 0.5 to 500 mg and most preferably between about 1 and 200 mg. A daily dose of about 0.01 to 100 mg/kg body weight, preferably between about 0.1 and about 50 mg/kg body weight, may be appropriate. The daily dose can be administered in one to four doses per day.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Preparation of Compounds

Compounds of the invention may be synthesized by synthetic routes that include processes similar to those well known in the chemical arts, particularly in light of the description contained herein. The starting materials are generally available from commercial sources such as Aldrich Chemicals (Milwaukee, Wisconsin, USA) or are readily prepared using methods well known to those skilled in the art (e.g., prepared by methods generally described in Louis F. Fieser and Mary Fieser, Reagents for Organic Synthesis, v. 1-19, Wiley, New York, (1967-1999 ed.); Alan R. Katritsky, Otto Meth-Cohn, Charles W. Rees, Comprehensive Organic Functional Group Transformations, v 1-6, Pergamon Press, Oxford, England, (1995); Barry M. Trost and Ian Fleming, Comprehensive Organic Synthesis, v. 1-8, Pergamon Press, Oxford, England, (1991); or Beilsteins Handbuch der organischen Chemie, 4, Aufl. Ed. Springer-Verlag, Berlin, Germany, including supplements (also available via the Beilstein online database)).

A computer-aided drug design focused on a small molecule library was used to select most potent and drug like inhibitor of CD38 NADase activity for further study. In one aspect the following synthetic route may be used.

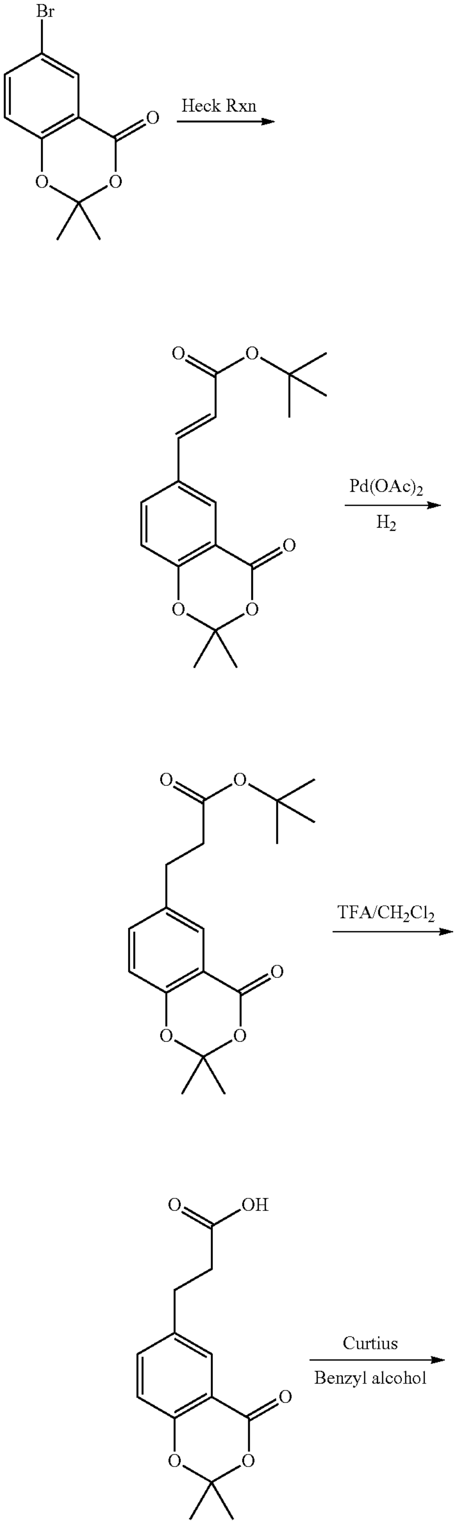

-continued

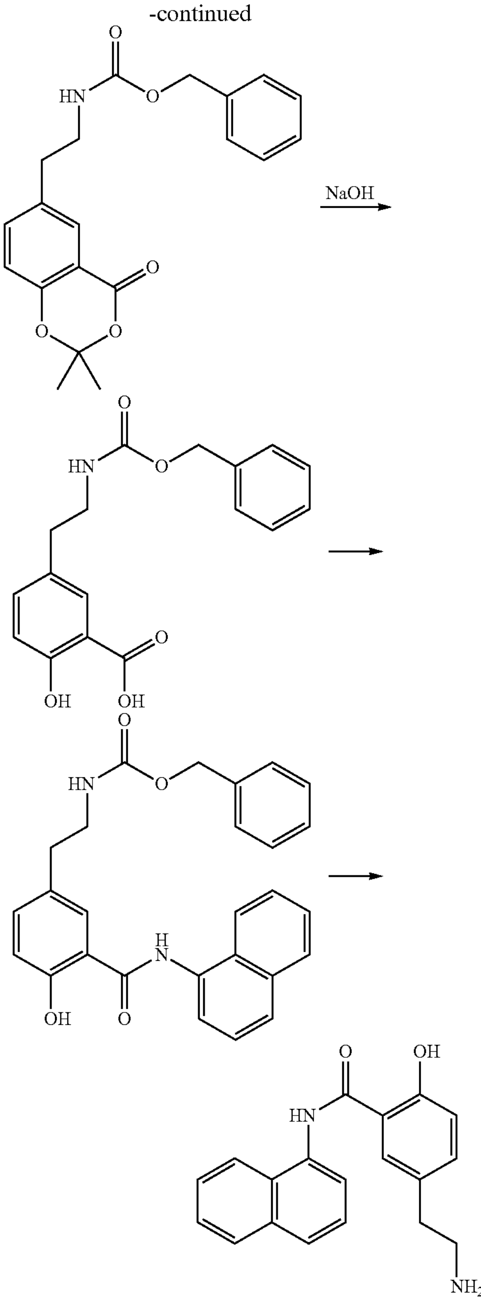

For further discussion of the preparation of the compounds of the present invention, see the synthetic examples provided herein.

Methods of Using NAD Modulators

Another aspect of the present disclosure provides a method of increasing intracellular NAD levels in a subject in need thereof, comprising administering an effective amount of a compound according to formula I or formula II to the subject. A subject can be characterized as being in need of increased intracellular NAD levels if they have, or have an increased risk of having, a disease or disorder associated with lower intracellular NAD levels, or a disease or disorder that can be treated by increasing intracellular NAD levels. The compounds disclosed herein act as NAD modulating compounds. The compounds affect NAD levels by inhibiting NADases, such as CD38 or CD157, which degrade NAD. CD38 and CD157 are similar enzymes that share a high degree of homology. In some embodiments, the compounds inhibit CD38. See Chini et al., Trends Pharmacol Sci., 39(4):424-436 (2018).

Because of their ability to modulate (e.g., increase) NAD levels, the compounds described herein can be used to treat diseases and conditions that show a dependence on NAD and/or CD38 levels in the body. See Hong et al., Front Cell Dev Biol., 8:246 (2020). For example, it has been shown that CD38 plays an active role in the age-related NAD decline in mammals. Thus, the compounds disclosed herein can be used to delay aging and can be used in the prevention of age-related senescence and replicative exhaustion. Chini et al., Mol Cell Endocrinol., 455:62-74 (2017). CD38 and NAD have also been shown to play an important role in neurodegeneration and neuroinflammation. Guerreiro et al., Cells, 9(2):471 (2020). Accordingly, in some embodiments, the compounds can be used to treat a subject having a degenerative disease.

The compounds disclosed herein can also be used in the maintenance and expansion of hematopoietic and mesenchymal stem cells. M. Xiao and D. C. Dooley, Leuk Lymphoma 38(5-6); 489-97 (2000). Accordingly, in some embodiments the compounds can be used to treat bone marrow failure. The CD38 inhibitors can also be used as radioprotectants, based on the ability of hydroxy salicylamides to protect against UV radiation, etc.

The CD38 inhibitors disclosed herein can also be used to treat and/or prevent certain types of cancer including myeloma and lymphoma. Costa et al., Cells, 8(12):1632 (2019). Myeloma is a type of cancer that begins in the bone marrow and is a cancer of B lymphocytes of the plasma. Examples of myeloma include multiple myeloma, which is by far the most common type of melanoma; plasmacytoma, in which only one site (e.g., tumor) of myeloma cells evident in the body; localized myeloma, which is found in one site with exposure to neighboring sites; and extramedullary myeloma, in which the melanoma occurs in a tissue other than the marrow, such as the skin, muscles or lungs.

In some embodiments the NAD modulators (e.g., CD38 inhibitors) can be used to treat infection, such as tuberculosis infection and intracellular mycobacterial infections. In some instances, the CD38 inhibiting compounds may be used to treat HIV. See Savarino et al., AIDS, 14(9):1079-89 (2000). In other instances, the CD38 inhibiting compounds may be used to treat COVID-19. Horenstein et al., Physiol Rev., 101(4):1457-1486 (2021).

Examples have been included to more clearly describe particular embodiments of the invention. However, there are a wide variety of other embodiments within the scope of the present invention, which should not be limited to the specific examples provided herein.

EXAMPLES

1. 3D-Docking Simulation

Figure 1:
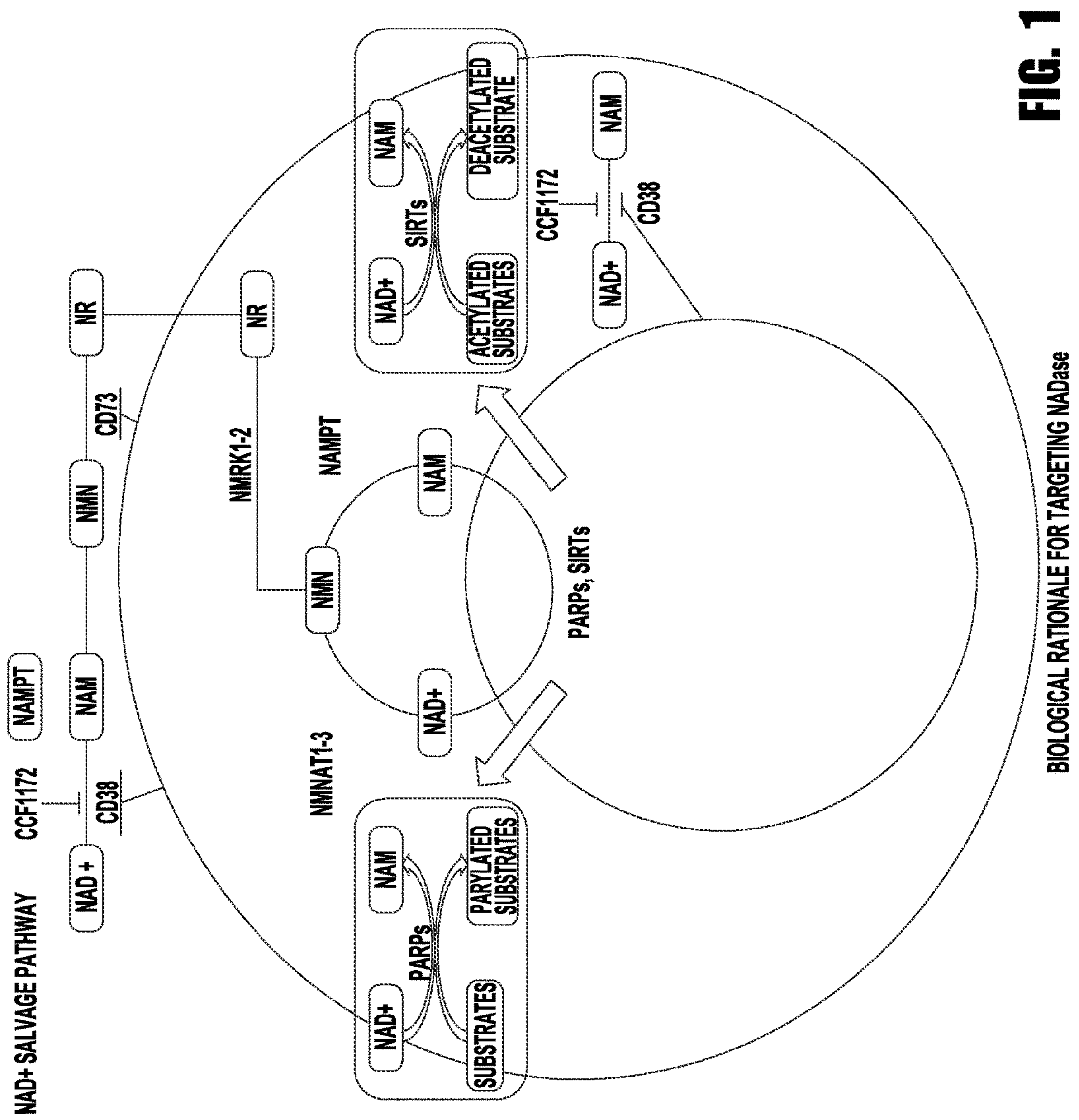
FIG. 1 provides a schematic representation of the NAD+ Salvage pathway, which supports the biological rationale for targeting NADase.
Figures 2A, 2B:
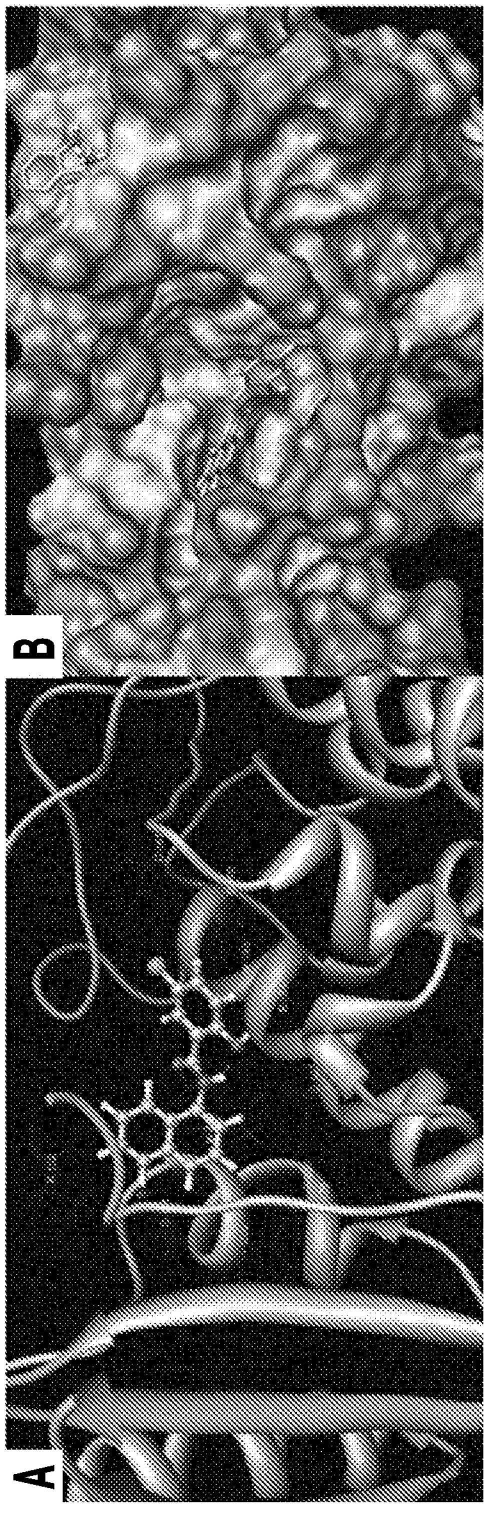
FIGS. 2A and 2B provide images showing provides diagrams showing Interactions of 1-17 in the CD38 binding pocket. Unbiased docking simulation of 3D optimized structure of compound 1-17 was performed using against 2000 different human proteins structure in protein data bank, highest scoring proteins were selected and further refined.
Figures 3A, 3B, 3C, 3D:
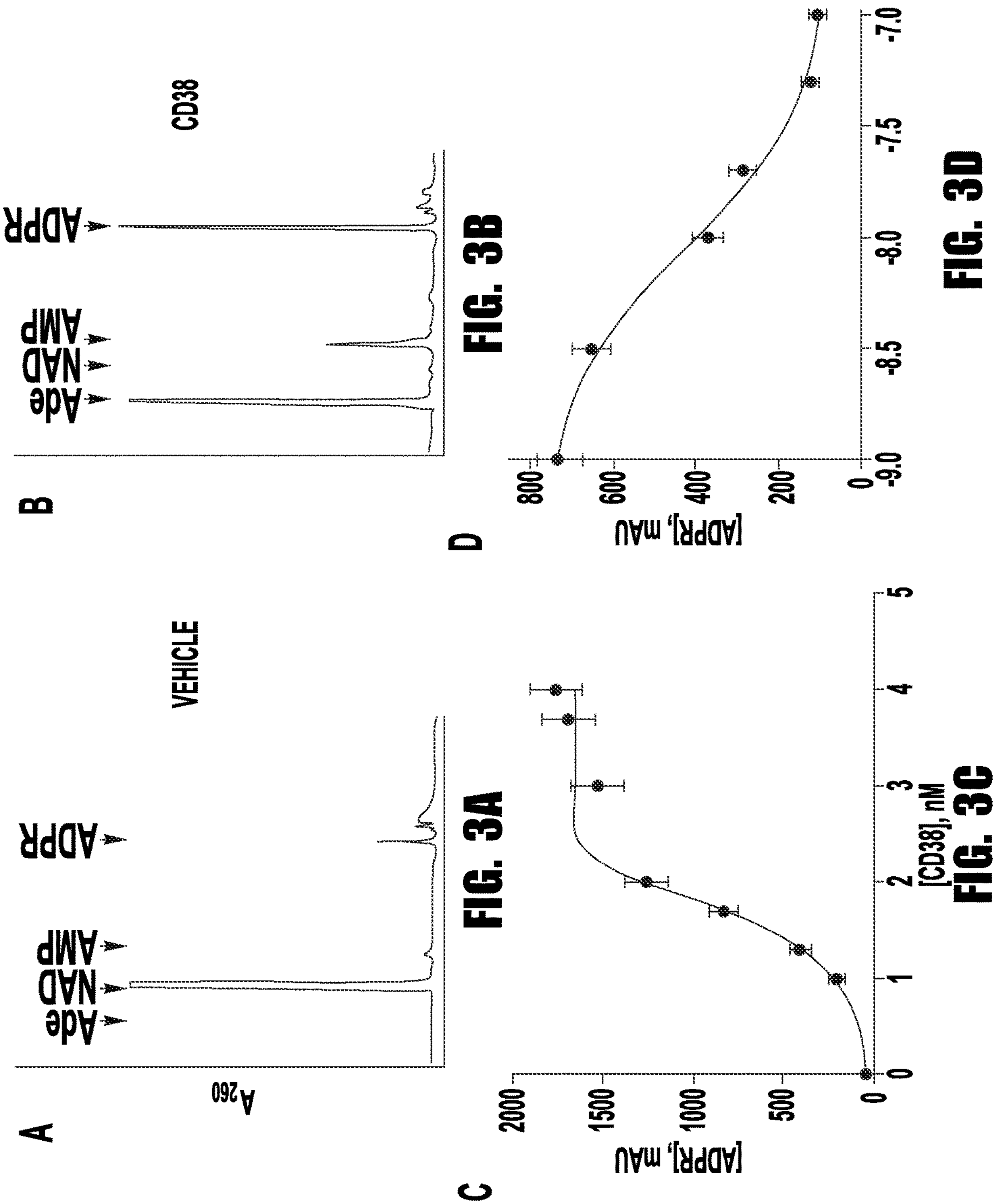

Unbiased 3D-docking simulation was performed using the 3D optimized structure of compound 1-17 against 2000 different human protein structures in the protein data bank. The highest scoring proteins were selected and further refined. CD38 was the highest scoring protein. FIG. 2 shows the interactions of compound 1-17 in the CD38 binding pocket. The complex was energy minimized using Chimera 1.8.0.

Overview of the experiments described in Examples 2-6.

The effects of CD38 inhibitor 1-17 and its analogues on hematopoiesis of healthy murine bone marrow were tested. A 40 mg/kg treatment dose was used, which was determined to be effective and well tolerated. Experiments were conducted to determine whether treatment with compound 1-17 has impact on blood counts and NAD+ levels in cells. The inventors treated 9 mice which were sacrificed at 2, 5 and 12 week and blood counts, marrow morphology and cellularity and bone marrow colony formation per $10^6$ cell were determined in colony forming assays.

We will also measure the content of LSK cells in the marrow using flow cytometry. We will also evaluate CD38 inhibitor's abilities to a) improve engraftment of murine cells using competitive repopulation assays using in vitro and in vivo treated murine HSCS and b) following recovery after radiation-induced HSPC injury.

The effects of CD38 inhibitors were evaluated in competitive transplantation assays of CD45.1 or CD45.2 bone marrow cells mixed at 50:50 ratio to be transplanted into lethally irradiated ROSA mice. In reciprocal experiments either CD45.1 or CD45.2 will be treated. To distinguish from impact autologous recovery on results, transplant will be perform into either CD45.1 or CD45.2 irradiated recipients thus effectively the experiment will be repeated (8 mice per treatment group and condition). Recipient autologous recovery will be distinguished by red florescence. The readout will include skewed repopulation towards CD38 inhibitor treated graft.

A second assay will include measurement of hematopoietic recovery following radiation injury as a model of HSC deficiency. 3 different strains of mice (6 group: 12 mice per strain) will be sub-lethally irradiated and treated starting from day one with CD38 inhibitor administrated via ip injection (5 days per week). We will monitor mice weight, and determine blood counts at 4 and 10 weeks post irradiation. Cellularity of the marrow will be determined in 2 mice scarified 3 weeks post irradiation.

Depending on the outcomes of experiments, we will repeat these experiments using combinations of CD38 inhibitors with other agents like nicotinamide to determine synergistic effects in vivo.

2. β-NAD+ Degradation Assay

The dose dependent inhibition of CD38 enzymatic activity by compounds 1-17 and 1-11 was investigated. The recombinant human CD38 full length protein UniProtKB—P28907 (CD38_HUMAN) was cloned into pET28a and purified using IMAC column followed by gel filtration on SephacrylS200. The purified protein (10 μg/ml) was incubated with varying amount of NAD+ in assay buffer (50 HEPES, 5 mM MgCl2 at pH 7.0) at 25° C. for 3 hours, reaction was stopped by heat inactivation followed by acetone precipitation of protein the supernatant was vacuum dried and dissolved in water and loaded onto reverse phase C18 column and eluted with a gradient of 0-25% of acetonitrile in water. As shown in FIG. 3, the peak area of various product was estimated and plotted as the function of enzyme or small molecule concentration.

FIG. 3 shows that compound 1-17 inhibits CD38 and protects NAD+ degradation in vitro. Full length wild type recombinant CD38 was expressed and purified and incubated with NAD+ and high-performance liquid chromatographic assay using $C_{18}$ were used to quantify NAD+ degradation.

3. Cell Proliferation Assay

FIG. 4 demonstrates that NAD+ protection by compound 1-17 extends the life span of undifferentiated normal human fibroblast (NHFB) under in-vitro cell culture conditions. NHFB were either young (<8 doubling time) (FIG. 4A) or old (>10 doublings) (FIG. 4B). Cell cultures were treated with the indicated amount of 1-17 in complete growth media. The doubling time significantly increased in a dose dependent fashion.

4. Mouse HSPC Self Renewal

The murine bone marrow cells from $C_{57}$bl6 mice were grown in methyl cellulose in the presence and absence of compound 1-17. Colony numbers were counted every week and re-plated.

FIG. 5 provides graphs showing that treatment with compound 1-17 increases mouse HSPC self-renewal. As shown in FIG. 5A, the treatment of Mouse bone marrow markedly increased the self-renewal of HSPCs in colony numbers as well as in overall cell counts. Additionally, as shown in FIG. 5B directed to total cellular output, cells also proliferate far longer than the vehicle control, maintaining population for an average of 1 to 2 passes after control.

5. Human HSPC Self Renewal

Human bone marrow cells from healthy volunteers were grown in methyl cellulose in the presence and absence of the compound 1-17 and colony number were counted after eight days in culture and re-plated till control HSPCs were completely exhausted. As shown in FIG. 6, treatment using compounds 1-17 and 1-11 expands the colony forming hematopoietic stem and progenitor cells (HSPCs).

6. Stem Cell Function

Total Human bone marrow, isolated CD34+ HSPCs, and long-term culture initiating hematopoietic cells (LTC-IC), were grown in the presence and absence of compound 1-17 and the total cellular output was determined. As shown in FIG. 7, treatment with compound 1-17 expands long term hematopoietic stem cells in cell culture. Compound 1-17 synergies with NAD treatment.

7. Activity of Additional CD38 Inhibitors

The kinetics of inhibition of a variety of CD38 inhibitors have been determined by the inventors. The determination of the inhibition equilibrium constant Ki is shown in FIG. 8. FIG. 8A provides a graph showing the kinetics of CD38 activity in the presence of different concentrations of the inhibitors, while FIG. 8B shows calculation of Ki from the slope of the semi log fit curve of the velocity, determined by reaction progress curve at different inhibitor concentrations. FIG. 8C provides the structures of a number of the compounds that were tested.

8. Synthesis of Compound 1-18 (2-hydroxy-N-(naphthalen-1-yl)-5-(trifluormethyl)benzamide)

Procedure Step 1

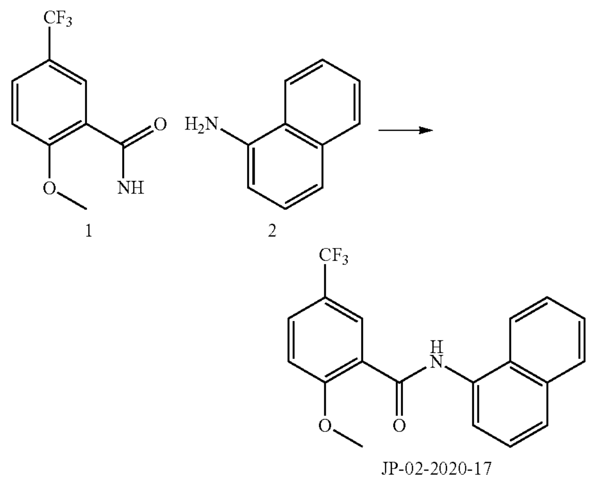

1 2

JP-02-2020-17

2-methoxy-5-trifluoromethyl benzoic acid (1, 2.0 g, 9.08 mmoles) was dissolved in dry DMF (20 ml) at rt under $N_2$. Hunig's base (3.17 ml, 18.17 mmoles) was added followed by HATU (3.62 g, 9.54 mmoles). After stirring for 15 minutes, 2-Amino-napthalene (2, 1.23 g, 8.63 mmoles) was added. The reaction was stirred at 20° C. for 18 hr after which time ethyl acetate (100 ml) and 70 ml of saturated sodium chloride solution were added. The organic layer was separated and washed with saturated sodium chloride solution (3×70 ml). The organic layer was separated, dried over $MgSO_4$, filtered, and concentrated by rotary evaporation. The crude product was purified by flash silica gel chromatography using ethyl acetate/hexanes (2:8) and gave 1.803 g (57%) of white solid.

Procedure Step 2

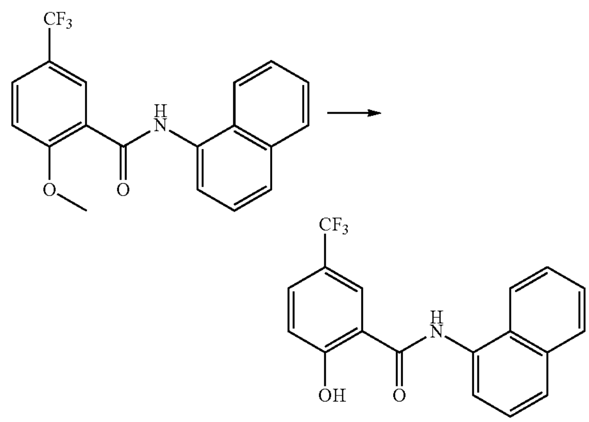

The methoxy derivative 2-Methoxy-N-(naphthalen-1-yl)-5-(trifluoromethyl)benzamide (0.77 g, 2.23 mmoles) was dissolved in dry dichloromethane (20 ml) at 20° C. under nitrogen gas. The reaction was then cooled to −78° C. and $BBr_3$ (2.3 ml, 1.M in hexanes) was added dropwise. After stirring at −78° C. for 1.5 hr the reaction mixture was warmed to 0° C. with continued stirring for 3 hr. The reaction was added to ice water and extracted with ethyl acetate (100 ml) The organic layer was separated, washed with saturated sodium chloride solution (50 ml), separated, dried over $MgSO_4$, filtered, and concentrated by rotary evaporation. Trituration with dichloromethane/hexanes (1:1) 15 ml gave 0.6 g (81%) of a white solid.

9. Synthesis of Compound 1-17 (5-(2-Aminoethyl)-2-hydroxy-N-(naphthalen-1-yl)benzamide)

Procedure Step 1

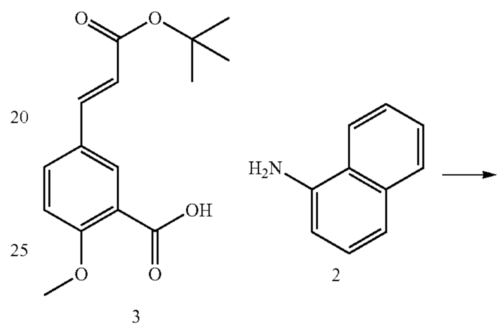

3 2

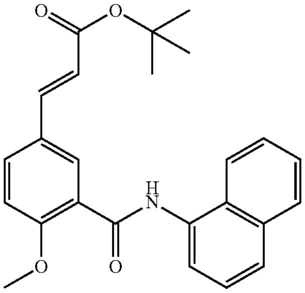

JP-02-2020-15

(E)-5-(3-(Tert-butoxy)-3-oxoprop-1-en-1-yl)-2-methoxybenzoic acid (3, 0.62 g, 2.23 mmoles) was dissolved in dry DMF (5 ml) at rt under $N_2$. Hunig's base (0.77 ml, 4.46 mmoles) was added followed by HATU (0.93 g, 2.45 mmoles). After stirring for 15 minutes, 2-Amino-napthalene (2, 0.32 g, 2.23 mmoles) was added. The reaction was stirred at rt for 18 hr after which time ethyl acetate (100 ml) and 70 ml of saturated sodium chloride solution were added. The organic layer was separated and washed with saturated sodium chloride solution (3×70 ml). The organic layer was separated, dried over $MgSO_4$, filtered, and concentrated by rotary evaporation. The crude product was purified by flash silica gel chromatography using ethyl acetate/hexanes (2:8) and gave 0.52 g of white solid.

Procedure Step 2

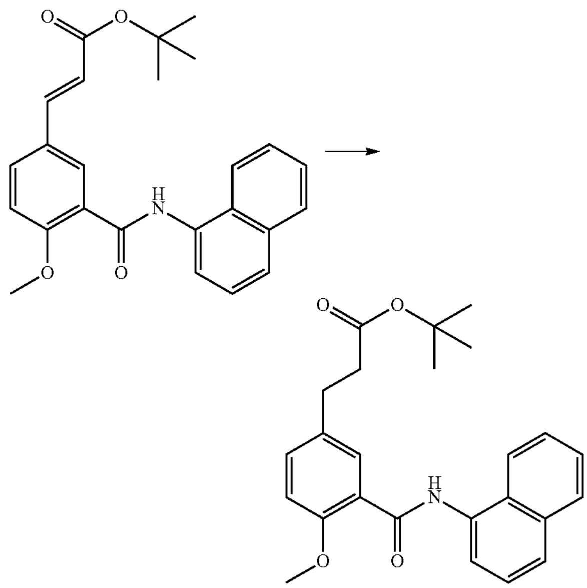

Tert-butyl (E)-3-(4-methoxy-3-(naphthalen-1-ylcarbamoyl)phenyl)acrylate (0.50 g, 1.24 mmoles) was dissolved in absolute ethanol (20 ml) at 20° C. Ammonium formate (0.39 g, 6.20 mmoles) was added. The reaction mixture was degassed and purged with $N_2$ 2× followed by addition of $Pd(OH)_2$ (0.05 g, 20% wt %) and then heated at 80° C. for 1.5 hr. The reaction mixture was cooled, filtered through celite to remove the catalyst, and concentrated by rotary evaporation. The mixture remaining was partitioned between $CH_2Cl_2$ (50 ml) and water (10 ml), the organic layer separated, dried over $MgSO_4$, filtered, and concentrated by rotary evaporation to give 0.46 g (91%) of brown oil which was used without further purification.

Procedure Step 3

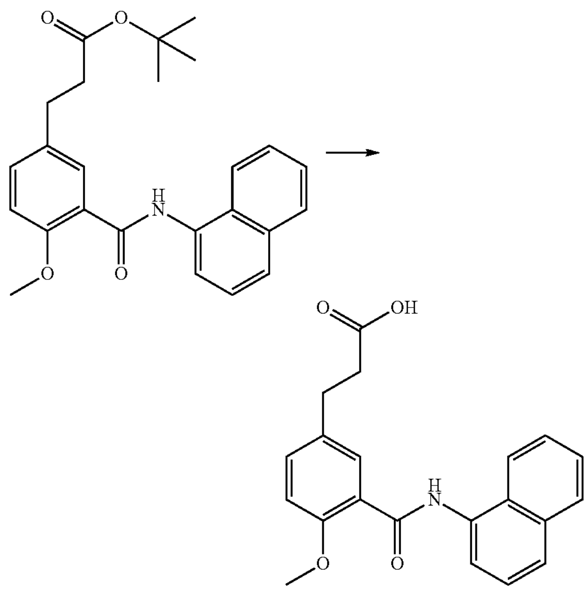

The saturated Tert-butyl 3-(4-methoxy-3-(naphthalen-1-ylcarbamoyl)phenyl)propanoate (0.406 g, 1.0 mmoles) was dissolved in $CH_2Cl_2$ (4 ml) at 20° C. Triethylsilane (0.40 ml, 2.5 mmoles) was added followed by 6 ml of a 1:1 mix of Trifluoroacetic acid/$CH_2Cl_2$. The reaction was stirred for 3 hr and then concentrated by rotary evaporation which gave 0.34 g (90%) of white solid.

Procedure Step 4

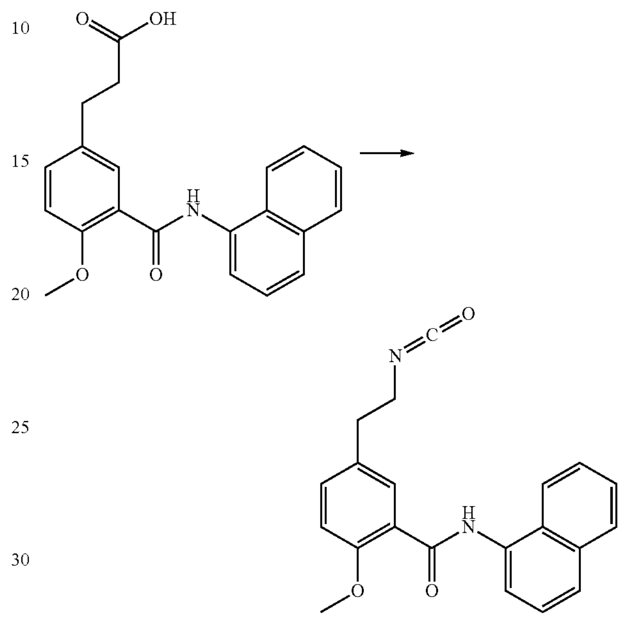

To a mixture of 3-(4-methoxy-3-(naphthalen-1-ylcarbamoyl)phenyl)propanoic acid (0.36 g, 1.03 mmoles), Triphenylphosphine (0.54 g, 2.06 mmoles), and $NaN_3$ (0.08 g, 1.23 mmoles) in dry $CH_3CN$ (30 ml) at 20° C. was added $C_{13}CN$ (0.21 ml, 2.06 mmoles) dropwise via syringe. The reactants were allowed to react for 2 hr. After concentration of the reaction mixture by a rotary evaporator, the residue was then diluted with $CH_2Cl_2$ (20 mL) and washed with $H_2O$ (5 mL). The organic layer was separated, dried over anhydrous $MgSO_4$, filtered, and concentrated. The crude acyl azide was dissolved in dry toluene (10 ml) and heated at 80° C. under nitrogen gas for 1 hr. The reaction was cooled and concentrated by rotary evaporation to give 0.327 g (91%) of crude isocyanate, waxy brown solid. This was used without further purification.

Procedure Step 5

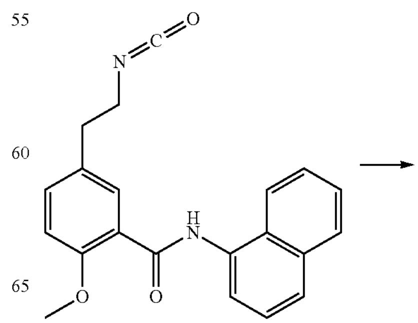

-continued

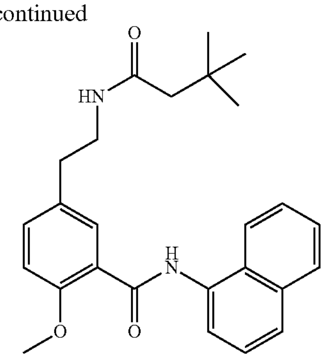

To a THF (10 ml) solution of sodium tert-butoxide (0.103 g, 0.98 mmoles) and tert-butanol (0.165 ml, 1.96 mmoles) at 0° C. under nitrogen gas was added a THE (10 ml) solution of 5-(2-Isocyanatoethyl)-2-methoxy-N-(naphthalen-1-yl) benzamide (0.327 g, 0.98 mmoles). The reaction was stirred at 0° C. for 2 hours, and then warmed to 20° C. with continued stirring for 1 hr. The reaction was quenched with saturated ammonium chloride solution (10 ml) and extracted with ethyl acetate (30 ml). The organic layer was separated, dried over $MgSO_4$, filtered, and concentrated. Flash silica gel chromatography with ethyl acetate/hexanes gave 0.14 g (91%) of the N—BOC protected derivative, a yellow waxy solid.

Procedure Step 6

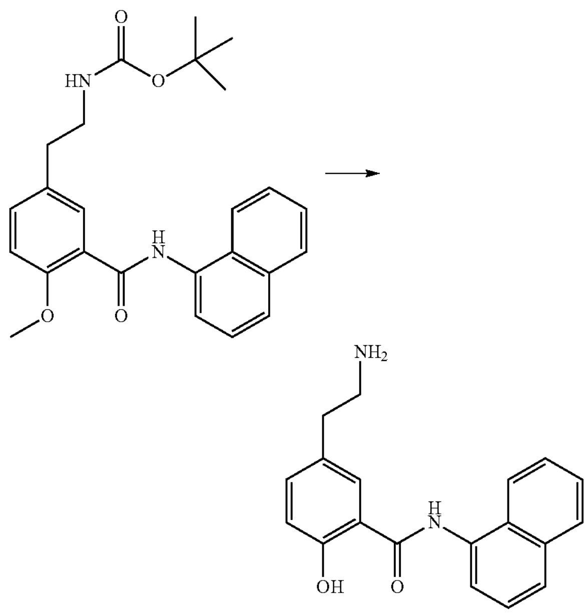

To the Tert-butyl (4-methoxy-3-(naphthalen-1-ylcarbamoyl)phenethyl)carbamate (0.118 g, 0.28 mmoles) was added 5 ml of 4N HCl in dioxane at 20° C. The reaction was stirred for 3 hr and then concentrated by rotary evaporation to give the corresponding amine HCl salt, a white solid. This salt was suspended in $CH_2Cl_2$ (10 ml), the mixture cooled to 0° C. under nitrogen gas, and then $BBr_3$ (1.15 ml, 1.0M in hexanes) was added. The reaction was stirred for 16 hr warming to 20° C. The reaction was then cooled to 0° C., treated with saturated sodium bicarbonate solution (10 ml) for 30 minutes and the precipitate collected by filtration. The solid was washed with water (10 ml), redissolved in 20 ml of $CH_2Cl_2$/$CH_{30}H$ (8:2), dried over $MgSO_4$, filtered, and concentrated to give 41 mg (51%) of a light beige solid.

10. Synthesis of Compound 1-19 ((E)-3-(4-Hydroxy-3-(naphthalen-1-ylcarbamoyl)phenyl)acrylic acid)

Procedure 1

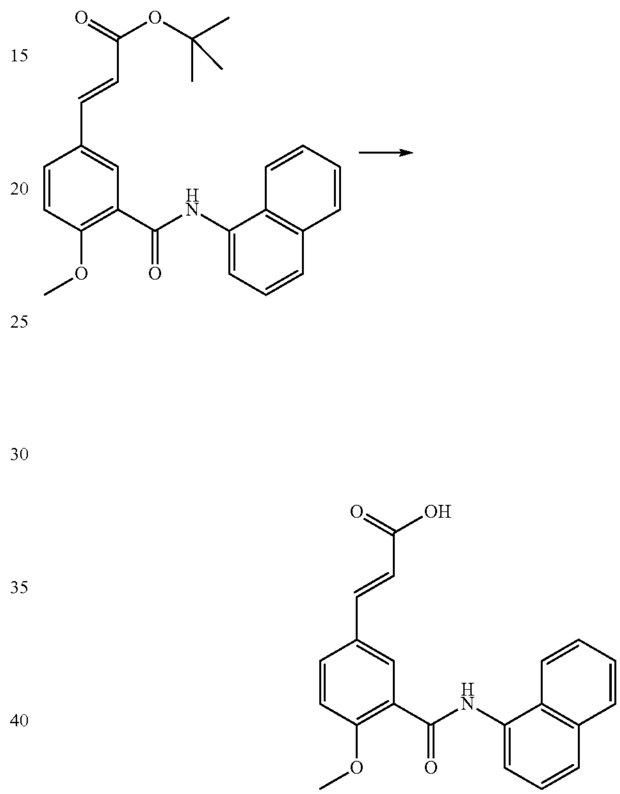

The Tert-butyl (E)-3-(4-methoxy-3-(naphthalen-1-ylcarbamoyl)phenyl)acrylate (0.224 g, 0.55 mmoles) was dissolved in dry $CH_2Cl_2$ (10 ml) at 20° C. Trifluoroacetic acid (10 ml) was added and the reaction stirred for 2 hr. Concentration by rotary evaporation gave 0.123 g (63%) of a light brown solid which was used without further purification.

Procedure 2

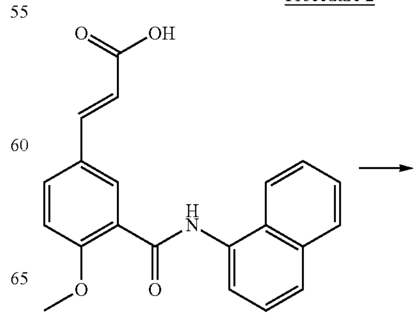

-continued

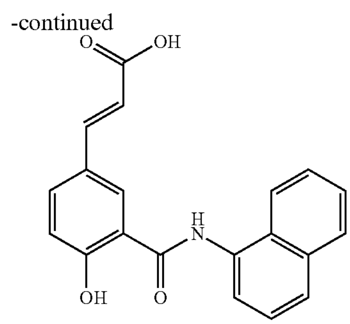

To (E)-3-(4-Hydroxy-3-(naphthalen-1-ylcarbamoyl)phenyl)acrylic acid (0.123 g, 0.354 mmoles) suspended in dry $CH_2Cl_2$ at 0° C. under $N_2$ was added $BBr_3$ (1.41 ml, 1.41 mmoles, 1 M in hexanes) was added via syringe. The reaction mixture was stirred for 16 hr warming to 20° C. The reaction mix was added to ice water, stirred for 1 hr, and the solid precipitate collected by filtration. The solid was washed with water (25 ml) and dried by toluene azeotrope (2×50 ml). This gave 0.075 g of a light brown solid.

The complete disclosure of all patents, patent applications, and publications, and electronically available materials cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A compound having the structure

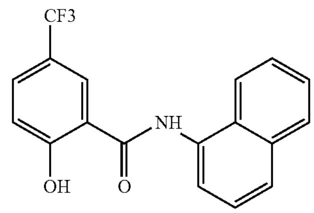 [SMILES: O=C(Nc1cccc2ccccc12)c1cc(C(F)(F)F)ccc1O]

or a pharmaceutically acceptable salt thereof.

* * * * *